United States Patent

Andree et al.

Patent Number: 5,250,498
Date of Patent: Oct. 5, 1993

[54] HERBICIDAL 2-IMINOPYRIDINES

[75] Inventors: Roland Andree, Langenfeld; Hauke Fürstenwerth, Leverkusen; Klaus Jelich, Wuppertal; Gunther Beck, Leverkusen; Peter Babczinski, Wuppertal; Klaus Lürssen, Bergisch Gladbach; Hans-Joachim Santel, Leverkusen; Robert R. Schmidt, Bergisch Gladbach, all of Fed. Rep. of Germany

[73] Assignee: Bayer Aktiengesellschaft, Leverkusen, Fed. Rep. of Germany

[21] Appl. No.: 624,022

[22] Filed: Dec. 7, 1990

[30] Foreign Application Priority Data

Dec. 14, 1989 [DE] Fed. Rep. of Germany ....... 3941233
Jul. 5, 1990 [DE] Fed. Rep. of Germany ....... 4021439

[51] Int. Cl.$^5$ ............... C07D 207/20; A01N 47/18
[52] U.S. Cl. ................. 504/105; 546/275; 546/277; 546/280; 546/284; 546/304; 546/312
[58] Field of Search ........... 546/309, 275, 277, 280, 546/284, 304, 312; 71/94, 90, 92; 504/105

[56] References Cited

FOREIGN PATENT DOCUMENTS 0053011 6/1982 European Pat. Off. ............ 71/94
0259738 3/1988 European Pat. Off. ........... 546/309

OTHER PUBLICATIONS

Chemical Abstracts, vol. 98, Abstract 4.464a, p. 401, (Jan. 3, 1983), Inokuma et al.
Teotino et al, "Preparation and properties of 1-(aralkyl)-2-pyridonimines", Chem. Abstrs., vol. 64, 1966, pp. 9675h–9677b. Farmaco (Pavia) Ed. Sci. 17(12).
7429r: Shiokawa et al, "Preparation 3-cyanobenzyl-substituted heterocycles . . . ", Chem. Abstrs., vol. 111, 1989, Heterocycles, p. 715.

Primary Examiner—C. Warren Ivy
Assistant Examiner—Zinna N. Davis
Attorney, Agent, or Firm—Sprung Horn Kramer & Woods

[57] ABSTRACT

A method of combating unwanted vegetation which comprises applying to such vegetation or to a locus from which it is desired to exclude such vegetation, a herbicidally effective amount of a 2-iminopyridine of the formula

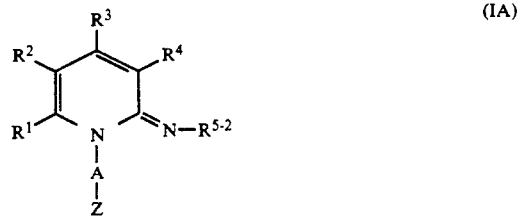

in which
$R^1$, $R^2$, $R^3$ and $R^4$ independently of one another represent hydrogen, halogen, alkyl, halogenoalkyl, alkoxy, halogenoalkoxy, alkylthio or halogenalkylthio,
$R^{5'}$ represents cyano, alkylcarbonyl, alkenylcarbonyl, alkynylcarbonyl, halogenoalkylcarbonyl, halogenoalkenylcarbonyl, halogenoalkynylcarbonyl, alkoxycarbonyl or alkylthiocarbonyl, or represents in each case optionally substituted phenylcarbonyl or phenoxycarbonyl, or represents alkylsulphonyl or optionally substituted phenylsulphonyl, or represents alkylaminocarbonyl or optionally substituted phenylaminocarbonyl, phenylalkylcarbonyl, phenylalkenylcarbonyl, furylcarbonyl, phenoxyalkylcarbonyl, thienylcarbonyl or pyridylcarbonyl, or represents cycloalkylcarbonyl, alkoxyalkylcarbonyl, alkylcarbonyloxyalkylcarbonyl, alkoxycarbonylcarbonyl or halogenalkylsulphonyl,
A represents alkanediyl and
Z represents optionally substituted aryl or optionally substituted hetaryl.

Those compounds wherein $R^{5-2}$ is not cyano are new.

5 Claims, No Drawings

HERBICIDAL 2-IMINOPYRIDINES

The invention relates to the use of new and known 2-iminopyridine derivatives as herbicides, and to new 2-iminopyridine derivatives and to a plurality of processes for the their preparation.

It is known that certain pyridine derivatives such as, for example, N-(2,4-difluorophenyl)-2-[3-(trifluoromethyl)-phenoxy]-3-pyridinecarboxamide (disclosed in EP-A 53,011), have herbicidal activity. The herbicidal activity of these previously known compounds against problem weeds, as well as their tolerance by important crop plants, is, however, not entirely satisfactory in all fields of application.

Certain substituted iminopyridines are also known (cf. JP 63/287764, cited in CA 111(1): 7429r and EP-A 259,738). However, nothing is known about the herbicidal activity of these compounds.

In the present application, there are first described the new 2-iminopyridine derivatives of the formula (I) and subsequently the new and the known 2-iminopyridine derivatives of the formula (IA).

New 2-iminopyridine derivatives have been found, of the general formula (I)

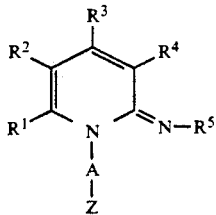

in which
R$^1$, R$^2$, R$^3$ and R$^4$ independently of one another represent hydrogen, halogen, alkyl, halogenoalkyl, alkoxy, halogenoalkoxy, alkylthio or halogenalkylthio,
R$^5$ represents alkylcarbonyl, alkenylcarbonyl, alkinylcarbonyl, halogenoalkylcarbonyl, halogenoalkenylcarbonyl, halogenoalkinylcarbonyl, alkoxycarbonyl or alkylthiocarbonyl, or represents in each case optionally substituted phenylcarbonyl or phenoxycarbonyl, or represents alkylsulphonyl or optionally substituted phenylsulphonyl, or represents alkylaminocarbonyl or optionally substituted phenylaniinocarbonyl, phenylalkylcarbonyl, phenylalkenylcarbonyl, furylcarbonyl, phenoxyalkylcarbonyl, thienylcarbonyl or pyridylcarbonyl, or represents cycloalkylcarbonyl, alkoxyalkylcarbonyl, alkylcarbonyloxyalkylcarbonyl, alkoxycarbonylcarbonyl or halogenalkylsulphonyl,
A represents alkanediyl and
Z represents optionally substituted aryl or optionally substituted hetaryl.

Furthermore, it has been found that new 2-iminopyridine derivatives of the general formula (I)

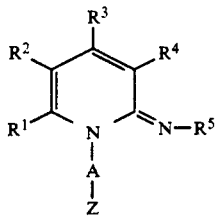

in which
R$^1$, R$^2$, R$^3$ and R$^4$ independently of one another represent hydrogen, halogen, alkyl, halogenoalkyl, alkoxy halogenoalkoxy, alkylthio or halogenalkylthio,
R$^5$ represents alkylcarbonyl, alkenylcarbonyl, alkinylcarbonyl, halogenoalkylcarbonyl, halogenoalkenylcarbonyl, halogenoalkinylcarbonyl, alkoxycarbonyl or alkylthiocarbonyl, or represents in each case optionally substituted phenylcarbonyl or phenoxycarbonyl, or represents alkylsulphonyl or optionally substituted phenylsulphonyl, or represents alkylaminocarbonyl or optionally substituted phenylaminocarbonyl, phenylalkylcarbonyl, phenylalkenylcarbonyl, furylcarbonyl, phenoxyalkylcarbonyl, thienylcarbonyl or pyridylcarbonyl, or represents cycloalkylcarbonyl, alkoxyalkylcarbonyl, alkylcarbonyloxyalkylcarbonyl, alkoxycarbonylcarbonyl or halogenalkylsulphonyl,
A represents alkanediyl and
Z represents optionally substituted aryl or optionally substituted hetaryl,
are obtained when 1,2-dihydropyridin-iminium salts of the general formula (II)

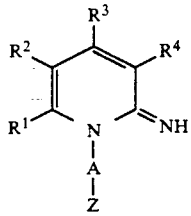

in which
R$^1$, R$^2$, R$^3$, R$^4$, A and Z have the abovementioned meanings and HX represents the equivalent of an inorganic or organic acid
(a) are reacted with halogen compounds of the general formula (III)

$$R^{5\text{-}1}\text{—}X^1 \qquad (III)$$

in which
R$^{5\text{-}1}$ represents alkylcarbonyl, alkenylcarbonyl, alkinylcarbonyl, halogenoalkylcarbonyl, halogenoalkenylcarbonyl, halogenoalkinylcarbonyl, alkoxycarbonyl or alkylthiocarbonyl, or represents in each case optionally substituted phenylcarbonyl or phenoxycarbonyl, or represents alkylsulphonyl or optionally substituted phenylsulphonyl, phenylalkylcarbonyl, phenylalkenylcarbonyl, furylcarbonyl, phenoxyalkylcarbonyl, thienylcarbonyl or pyridylcarbonyl, or represents cycloalkylcarbonyl, alkoxyalkylcarbonyl, alkylcarbonyloxyalkylcarbonyl, alkoxycarbonylcarbonyl or halogenalkylsulphonyl, and $X^1$ represents halogen, and, in the event that $R^{5-1}$ represents alkylcarbonyl, alkenylcarbonyl, alkynylcarbonyl, halogenoalkylcarbonyl, halogenoalkenylcarbonyl or halogenoalkinylcarbonyl, or represents optionally substituted phenylcarbonyl, with the corresponding carboxylic anhydrides, if appropriate in the presence of a base and if appropriate in the presence of a diluent, or (b) are reacted with isocyanates of the general formula (IV)

$$R^6-NCO \qquad (IV)$$

in which $R^6$ represents alkyl, or represents optionally substituted phenyl, if appropriate in the presence of a base and if appropriate in the presence of a diluent.

Finally, it has been found that the new and the known 2-iminopyridine derivatives of the general formula (I) and (IA), respectively, have very good herbicidal properties.

The invention also relates to the use of the new 2-iminopyridine derivatives of the formula (I) according to the invention and of the known 2-iminopyridine derivatives. The new and the known 2-iminonyridine derivatives come under the formula (IA) below:

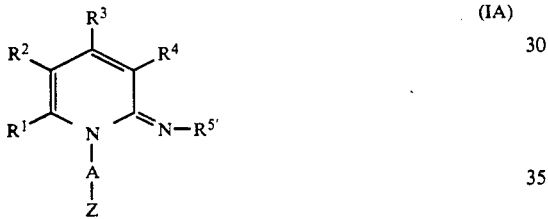

in which $R^1$, $R^2$, $R^3$ and $R^4$ independently of one another represent hydrogen, halogen, alkyl, halogenoalkyl, alkoxy or halogenoalkoxy, alkylthio or halogenalkylthio, $R^{5-2}$ represents cyano, alkylcarbonyl, alkenylcarbonyl, alkinylcarbonyl, halogenoalkylcarbonyl, halogenoalkenylcarbonyl, halogenoalkinylcarbonyl, alkoxycarbonyl or alkylthiocarbonyl, or represents in each case optionally substituted phenylcarbonyl or phenoxycarbonyl, or represents alkylsulphonyl or optionally substituted phenylsulphonyl, or represents alkylaminocarbonyl or optionally substituted. phenylaminocarbonyl phenylalkylcarbonyl, phenylalkenylcarbonyl, furylcarbonyl, phenoxyalkylcarbonyl, thienylcarbonyl or pyridylcarbonyl, or represents cycloalkylcarbonyl, alkoxyalkylcarbonyl, alkylcarbonyloxyalkylcarbonyl, alkoxycarbonylcarbonyl or halogenalkylsulphonyl, A represents alkanediyl and Z represents optionally substituted aryl or optionally substituted hetaryl.

The compounds of the formula (IA) can be prepared by processes (a) and (b), which have been described, and by known methods (cf., for example, EP-A 259,738).

Surprisingly, the 2-iminopyridine derivatives of the general formula (I) or (IA) according to the invention have a more powerful herbicidal potency against problem weeds than N-(2,4-difluorophenyl)-2-[3-(trifluoromethyl)-phenoxy]-3-pyridinecarboxamide, which is known from the prior art and represents a closely related compound chemically and from the point of view of its action.

Formula (I) provides a general definition of the 2-iminopyridine derivatives according to the invention. Preferred compounds of the formula (I) are those in which $R^1$, $R^2$, $R^3$ and $R^4$ independently of one another represent hydrogen, halogen, straight-chain or branched alkyl having 1 to 4 carbon atoms, straight-chain or branched halogenoalkyl having 1 to 4 carbon atoms, in each case straight-chain or branched alkoxy or alkylthio having 1 to 4 carbon atoms, or in each case straight-chain or branched halogenalkoxy or halogenalkylthio having 1 to 4 carbon atoms and 1 to 9 identical or different halogen atoms, $R^5$ represents straight-chain or branched alkylcarbonyl having 1 to 20 carbon atoms in the alkyl moiety, or represents in each case straight-chain or branched alkenylcarbonyl or alkynylcarbonyl each of which has 2 to 20 carbon atoms in the alkenyl or alkynyl moiety, or represents straight-chain or branched halogenoalkylcarbonyl having 1 to 20 carbon atoms in the alkyl moiety and 1 to 41 identical or different halogen atoms, or represents straight-chain or branched halogenoalkenylcarbonyl having 2 to 20 carbon atoms in the alkenyl moiety and 1 to 39 identical or different halogen atoms, or represents straight-chain or branched halogenoalkynylcarbonyl having 2 to 20 carbon atoms in the alkynyl moiety and 1 to 37 identical or different halogen atoms, or represents straight-chain or branched alkoxycarbonyl having 1 to 20 carbon atoms in the alkoxy moiety, or represents straight-chain or branched alkylthiocarbonyl having 1 to 20 carbon atoms in the alkylthio moiety, or represents phenylcarbonyl, phenoxycarbonyl, phenylaminocarbonyl, phenylmethylcarbonyl, phenylethylcarbonyl, phenylpropylcarbonyl, phenylethenylcarbonyl, furylcarbonyl, thienylcarbonyl, pyridylcarbonyl, phenoxymethylcarbonyl or phenoxyethylcarbonyl, each of which is optionally monosubstituted or polysubstituted by identical or different substituents, suitable phenyl substituents in each case being: halogen, cyano, nitro, straight-chain or branched alkyl having 1 to 4 carbon atoms, straight-chain or branched halogenoalkyl having 1 to 4 carbon atoms and 1 to 9 identical or different halogen atoms, straight-chain or branched alkoxy having 1 to 4 carbon atoms, and also straight-chain or branched halogenoalkoxy having 1 to 4 carbon atoms and 1 to 9 identical or different halogen atoms; $R^5$ furthermore represents straight-chain or branched alkylsulphonyl having 1 to 4 carbon atoms, or represents alkylaminocarbonyl having 1 to 20 carbon atoms in the straight-chain or branched alkyl moiety, or represents phenylsulphonyl which is optionally monosubstituted or polysubstituted by identical or different substituents, suitable phenyl substituents in each case being: halogen, cyano, nitro, straight-chain or branched alkyl having 1 to 4 carbon atoms, straight-chain or branched halogenoalkyl having 1 to 4 carbon atoms and 1 to 9 identical or different halogen atoms, straight-chain or branched alkoxy having 1 to 4 carbon atoms, straight-chain or branched halogenoalkoxy having 1 to 4 carbon atoms and 1 to 9 identical or different halogen atoms, and also alkoxycarbonyl having 1 to 4 carbon atoms in the straight-chain or branched alkoxy moiety, or represents cycloalkylcarbonyl having 3 to 6 carbon atoms in the cycloalkyl moiety, or represents straight-chain or branched alkoxyalkylcarbonyl having in each case 1 to 4 carbon atoms in the alkoxy- and alkyl moiety, or represents in each case straight-chain or branched alkylcarbonyloxalkylcarbonyl or alkoxycarbonylcarbonyl having 1 to 4 carbon atoms in the alkoxy- or alkyl moiety respectively, or represents straight-chain or branched halogenalkylsulfonyl having 1 to 4 carbon atoms and 1 to 9 identical or different halogen atoms, A represents straight-chain or branched alkanediyl having 1 to 4 carbon atoms and Z represents phenyl, pyridinyl, thienyl, thiazolyl, isothiazolyl, isoxazolyl or oxa-2,4-diazolyl, each of which is optionally monosubstituted or polysubstituted by identical or different substituents, suitable substituents in each case being: nitro, cyano, halogen, straight-chain or branched alkyl having 1 to 4 carbon atoms, in each case straight-chain or branched halogenoalkyl or halogenoalkylthio each of which has 1 to 4 carbon atoms and each of which has 1 to 9 identical or different halogen atoms, in each case straight-chain or branched alkoxy or alkylthio each of which has 1 to 4 carbon atoms, straight-chain or branched halogenoalkoxy having 1 to 4 carbon atoms and 1 to identical or different halogen atoms, straight-chain or branched alkoxycarbonyl having 1 to 4 carbon atoms in the alkoxy moiety, and also phenoxy which is optionally monosubstituted or polysubstituted by identical or different substituents from the series comprising halogen, $C_1$-$C_4$-alkyl and halogeno-$C_1$-$C_4$-alkyl.

Particularly preferred compounds of the formula (I) are those in which $R^1$ represents hydrogen, $R^2$ represents hydrogen, fluorine, chlorine, bromine, methyl, ethyl or trifluoromethyl, $R^3$ represents hydrogen, methyl, ethyl or trifluoromethyl, $R^4$ represents hydrogen, $R^5$ represents straight-chain or branched alkylcarbonyl having 1 to 10, preferably 1 to 5, carbon atoms in the alkyl moiety, or represents in each case straight-chain or branched alkenylcarbonyl or alkynylcarbonyl each of which has 2 to 10, preferably 2 to 5, carbon atoms in the alkenyl or alkynyl moiety, or represents straight-chain or branched halogenalkylcarbonyl having 1 to 10, preferably 1 to 4, carbon atoms and 1 to 21, preferably 1 to 9, fluorine and/or chlorine atoms, in particular trihalogemnethyl, or represents straight-chain or branched halogenalkenylcarbonyl having 2 to 10, preferably 2 to 4, carbon atoms in the alkenyl moiety and 1 to 19, preferably 1 to 3, fluorine and/or chlorine atoms, straight-chain or branched alkinylcarbonyl having 2 to 10, preferably 2 to 4, carbon atoms in the alkynyl moiety and 1 to 17, preferably 1 to 3, fluorine and/or chlorine atoms, or represents straight-chain or branched alkoxycarbonyl having 1 to 10, preferably 1 to 5, carbon atoms in the alkoxy moiety, or represents straight-chain or branched alkylthiocarbonyl having 1 to 10, preferably 1 to 5, carbon atoms in the alkyl moiety, or represents phenylcarbonyl, phenoxycarbonyl, phenylaminocarbonyl, phenylmethylcarbonyl, phenylethylcarbonyl, phenylpropylcarbonyl, phenylethenylcarbonyl, furylcarbonyl, thienylcarbonyl, pyridylcarbonyl, phenoxymethylcarbonyl or phenoxyethylcarbonyl, each of which is optionally monosubstituted or bisubstituted by identical or different substituents from the series comprising fluorine, chlorine, bromine, cyano, nitro, methyl, trifluoromethyl or methoxy, or represents methylsulphonyl or ethylsulphonyl, or represents straight-chain or branched alkylaminocarbonyl having 1 to 10, preferably 1 to 5, carbon atoms in the alkyl moiety, or represents phenylsulphonyl which is optionally monosubstituted or bisubstituted by identical or different substituents from the series comprising fluorine, chlorine, cyano, nitro, methyl, trifluoromethyl, methoxycarbonyl or ethoxycarbonyl, or represents $C_3$-$C_6$-cycloalkylcarbonyl, methoxyacetyl, acetyloxyacetyl or trifluormethylsulfonyl, A represents methanediyl or ethanediyl, in particular methanediyl, and Z represents phenyl, pyridinyl, thienyl, thiazolyl, isothiazolyl, isoxazolyl or oxa-2,4-diazolyl, each of which is optionally monosubstituted or disubstituted by identical or different substitutents, suitable substituents in each case being: nitro, cyano, fluorine, chlorine, bromine, methyl, ethyl, trifluoromethyl, difluoromethyl, methylthio, trifluoromethylthio, difluoromethylthio, methoxy, ethoxy, trifluoromethoxy, difluoromethoxy, methoxycarbonyl, ethoxycarbonyl and also phenoxy.

The preferred new and the preferred known 2-iminopipidine derivatives of the formula (IA) to be used according to the invention are those in which $R^1$, $R^2$, $R^3$ and $R^4$ independently of one another represent hydrogen, halogen, straight-chain or branched alkyl having 1 to 4 carbon atoms, straight-chain or branched halogenoalkyl having 1 to 4 carbon atoms and 1 to 9 identical or different halogen atoms, in each case straight-chain or branched alkoxy or alkylthio having 2 to 4 carbon atoms, or in each case straight-chain or branched halogenalkoxy or halogenalkylthio having 1 to 4 carbon atoms and 1 to 9 identical or different halogen atoms, represents cyano, straight-chain or branched alkylcarbonyl having 1 to 20 carbon atoms in the alkyl moiety, or represents in each case straight-chain or branched alkenylcarbonyl or alkynylcarbonyl each of which has 2 to 20 carbon atoms in the alkenyl or alkynyl moiety, or represents straight-chain or branched halogenoalkylcarbonyl having 1 to 20 carbon atoms in the alkyl moiety and 1 to 41 identical or different halogen atoms, or represents straight-chain or branched halogenoalkenylcarbonyl having 2 to 20 carbon atoms in the alkenyl moiety and 1 to 39 identical or different halogen atoms, or represents straight-chain or branched halogenoalkynylcarbonyl having 2 to 20 carbon atoms in the alkynyl moiety and 1 to 37 identical or different halogen atoms, or represents straight-chain or branched alkoxycarbonyl having 1 to 20 carbon atoms in the alkoxy moiety, or represents straight-chain or branched alkylthiocarbonyl having 1 to 20 carbon atoms in the alkyl moiety, or represents phenylcarbonyl, phenoxycarbonyl, phenylaminocarbonyl, phenylmethylcarbonyl, phenylethylcarbonyl, phenylpropylcarbonyl, phenylethenylcarbonyl, furylcarbonyl, thienylcarbonyl, pyridinylcarbonyl, phenoxymethylcarbonyl or phenoxyethylcarbonyl, each of which is monosubstituted or polysubstituted by identical or different substituents, suitable phenyl substituents in each case being: halogen, cyano, nitro, straight-chain or branched alkyl having 1 to 4 carbon atoms, straight-chain or branched halogenoalkyl having 1 to 4 carbon atoms and 1 to 9 identical or different halogen atoms, straight-chain or branched alkoxy having 1 to 4 carbon atoms, and also straight-chain or branched halogenoalkoxy having 1 to 4 carbon atoms and 1 to 9 identical or different halogen atoms; $R^{5'}$ furthermore represents straight-chain or branched alkylsulphonyl having 1 to 4 carbon atoms, or represents alkylaminocarbonyl having 1 to 20 carbon atoms in the straight-chain or branched alkyl moiety, or represents phenylsulphonyl which is optionally monosubstituted or polysubstituted by identical or different substituents, suitable phenyl substituents in each case being: halogen, cyano, nitro, straight-chain or branched alkyl having 1 to 4 carbon atoms, straight-chain or branched halogenoalkyl having 1 to 4 carbon atoms and 1 to 9 identical or different halogen atoms, straight-chain or branched alkoxy having 1 to 4 carbon atoms, straight-chain or branched halogenoalkoxy having 1 to 4 carbon atoms and 1 to 9 identical or different halogen atoms, and also alkoxycarbonyl having 1 to 4 carbon atoms in the straight-chain 6r branched alkoxy moiety, or represents cycloalkylcarbonyl having 3 to 6 carbon atoms in the cycloaklyl moiety, or represents straight-chain or branched alkoxyalkylcarbonyl having in each case 1 to 4 carbon atoms in the alkoxy- and alkyl moiety, or represents in each case straight-chain or branched alkylcarbonyloxalkylcarbonyl or alkoxycarbonylcarbonyl having 1 to 4 carbon atoms in the alkoxy- or alkyl moiety respectively, or represents straight-chain or branched halogenalkylsulphonyl having 1 to 4 carbon atoms and 1 to 9 identical or different halogen atoms, A represents straight-chain or branched alkanediyl having 1 to 4 carbon atoms, and Z represents phenyl, pyridinyl, thienyl, thiazolyl, isothiazolyl, isoxazolyl or oxa-2,4-diazolyl, each of which is optionally monosubstituted or polysubstituted by identical or different substituents, suitable substituents in each case being: nitro, cyano, halogen, straight-chain or branched alkyl having 1 to 4 carbon atoms, in each case straight-chain or branched halogenoalkyl or halogenoalkylthio each of which has 1 to 4 carbon atoms and each of which has 1 to 9 identical or different halogen atoms, in each case straight-chain: or branched alkoxy or alkylthio each of which has 1 to 4 carbon atoms, straight-chain or branched halogenoalkoxy having 1 to 4 carbon atoms and 1 to 9 identical or different halogen atoms, straight-chain or branched alkoxycarbonyl having 1 to 4 carbon atoms in the alkoxy moiety, and also phenoxy which is optionally monosubstituted or polysubstituted by identical or different substituents from the series comprising halogen, $C_1$–$C_4$-alkyl or halogeno-$C_1$–$C_4$-alkyl.

Particularly preferred compounds of the formula (IA) to be used according to the invention are those in which $R^1$ represents hydrogen, $R^2$ represents hydrogen, fluorine, chlorine, bromine, methyl, ethyl or trifluoromethyl, $R^3$ represents hydrogen, methyl, ethyl or trifluoromethyl, $R^4$ represents hydrogen, $R^{5'}$ represents cyano, straight-chain or branched alkylcarbonyl having 1 to 10, preferably 1 to 5, carbon atoms in the alkyl moiety, or represents in each case straight-chain or branched alkenylcarbonyl or alkylcarbonyl each of which has 2 to 10, preferably 2 to 5, carbon atoms in the alkenyl or alkynyl moiety, or represents straight-chain or branched halogenalkylcarbonyl having 1 to 10, preferably 1 to 4, carbon atoms and 1 to 21, preferably 1 to 9, fluorine and/or chlorine atoms, in particular trihalogenmethyl, or represents straight-chain or branched halogenalkenylcarbonyl having 2 to 10, preferably 2 to 4, carbon atoms in the alkenyl moiety and 1 to 19, preferably 1 to 3, fluorine and/or chlorine atoms, straight-chain or branched aflynylcarbonyl having 2 to 10, preferably 2 to 4, carbon atoms in the alkinyl moiety and 1 to 17, preferably 1 to 3, fluorine and/or chlorine atoms, or represents straight-chain or branched alkoxycarbonyl having 1 to 10, preferably 1 to 5, carbon atoms in the alkoxy moiety, or represents straight-chain or branched alkylthiocarbonyl having 1 to 10, preferably 1 to 5, carbon atoms in the alkyl moiety, or represents phenylcarbonyl, phenoxycarbonyl, phenylaminocarbonyl, phenylmethylcarbonyl, phenylethylcarbonyl, phenylpropylcarbonyl, phenylethenylcarbonyl, furylcarbonyl, thienylcarbonyl, pyridylcarbonyl, phenoxymethylcarbonyl or phenoxyethylcarbonyl, each of which is optionally monosubstituted disubstituted by identical or different substituents from the series comprising fluorine, chlorine, bromine, cyano, nitro, methyl, trifluoromethyl or methoxy, or represents methylsulphonyl or ethylsulphonyl or represents straight-chain or branched alkylaminocarbonyl having 1 to 10, preferably 1 to 5, carbon atoms in the alkyl moiety, or represents phenylsulphonyl which is optionally monosubstituted or bisubstituted by identical or different substitutents fi-om the series comprising fluorine, chlorine, cyano, nitro, methyl, trifluorinethyl, methoxycarbonyl or ethoxycarbonyl, or represents $C_3$–$C_6$-cycloalkylcarbonyl, methoxyacetyl, acetyloxyacetyl or trifluormethylsulphonyl, A represents methanediyl or ethanediyl, in particular methanediyl, and Z represents phenyl, pyridinyl, thienyl, thiazolyl, isothiazolyl, isoxazolyl or oxa-2,4-diazolyl each of which is optionally monosubstituted or bisubstituted by identical or different substituents, suitable substituents in each case being: nitro, cyano, fluorine, chlorine, bromine, methyl, ethyl, trifluoromethyl, difluoromethyl, methylthio, trifluoromethylthio, difluoromethylthio, methoxy, ethoxy, trifluoromethoxy, difluoromethoxy, methoxycarbonyl, ethoxycarbonyl and also phenoxy.

If, for example, N-[(3-trifluoromethyl)-benzyl]-5-methyl-2-iminopyridine hydrochloride and ethyl chloroformate are used as starting substances and triethylamine as the base, the course of the reaction of process (a) according to the invention may be represented by the following equation:

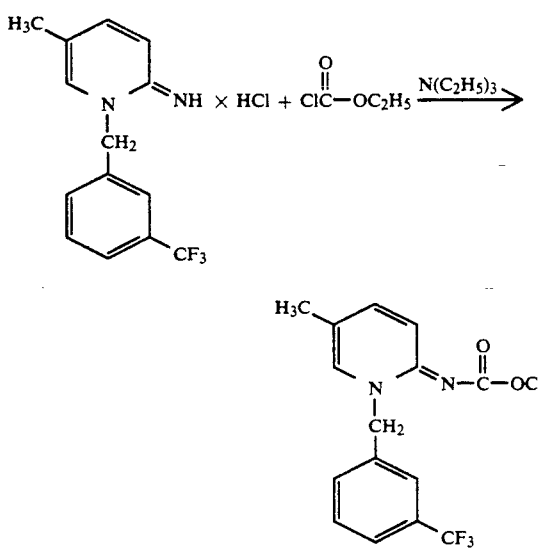

If, for example, N-[(3-trifluoromethyl)-benzyl]-5-methyl-2-iminopyridine hydrochloride and methylamine isocyanate are used, process (b) according to the invention may be represented by the following equation:

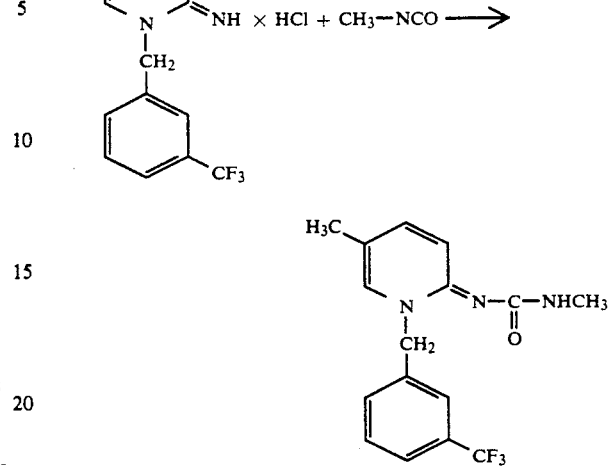

Formula (II) provides a general definition of the 1,2-dihydropyridin-iminium salts to be used as starting substances for the preparation of compounds of the formula (I) in processes (a) and (b) according to the invention.

In formula (II), $R^1$, $R^2$, $R^3$, $R^4$, A and Z preferably, or in particular, have those meanings which have already been mentioned above in connection with the description of the compounds of the formula (I) according to the invention as preferred, or as particularly preferred, for $R^1$, $R^2$, $R^3$, $R^4$, A and Z.

HX preferably represents the equivalent of a mineral acid such as, for example, hydrochloric acid or hydrobromic acid, or of a carboxylic acid such as, for example, oxalic acid.

Examples of starting substances of the formula (II) are listed in Table 1.

TABLE 1

| $R^1$ | $R^2$ | $R^3$ | $R^4$ | A | Z | HX |
|---|---|---|---|---|---|---|
| H | $CH_3$ | H | H | $-CH_2-$ | 3-Br-phenyl | HBr |
| H | Cl | H | H | $-CH_2-$ | 3-F-phenyl | HCl |
| H | Br | H | H | $-CH_2-$ | 3-$CF_3$-phenyl | HCl |
| H | $CH_3$ | H | H | $-CH_2-$ | 3-$NO_2$-phenyl | HCl |

TABLE 1-continued
| R¹ | R² | R³ | R⁴ | A | Z | HX |
|---|---|---|---|---|---|---|
| H | CH₃ | H | H | —CH₂— | 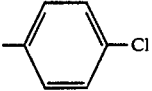 | HCl |
| H | CH₃ | H | H | —CH₂— | 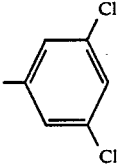 | HCl |
| H | F | CH₃ | H | —CH₂— | 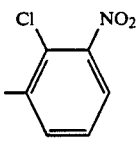 | HBr |
| H | C₂H₅ | CH₃ | H | —CH₂— | 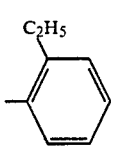 | HBr |
| H | CF₃ | CH₃ | H | —CH₂— | 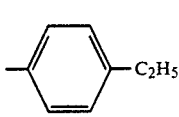 | HCl |
| H | CF₃ | C₂H₅ | H | —CH₂— | 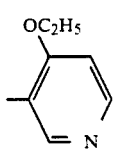 | HCl |
| H | C₂H₅ | C₂H₅ | H | —CH₂— | 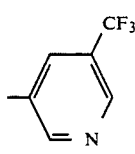 | HBr |
| H | F | C₂H₅ | H | —CH₂— | 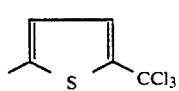 | HCl |
| H | F | CF₃ | H | —CH₂— | 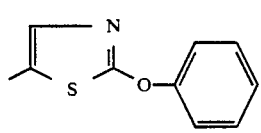 | HCl |
| H | C₂H₅ | CF₃ | H | —CH₂— | 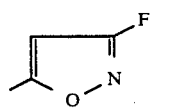 | HCl |
| H | CH₃ | CF₃ | H | —CH₂— | 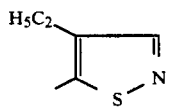 | HBr |
| H | Cl | CF₃ | H | —CH₂— | 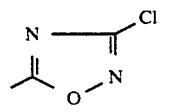 | HBr |

TABLE 1-continued

| R¹ | R² | R³ | R⁴ | A | Z | HX |
|---|---|---|---|---|---|---|
| H | CF₃ | CF₃ | H | —CH₂— | ![Z structure with N, O, N, CH₃, CH₃] | HCl |
| H | C₂H₅ | H | H | —CH₂— | ![Z structure with S, N, SCH₃] | HCl |
| H | C₂H₅ | CH₃ | H | —CH₂— | ![Z structure with S, SCH₃] | HBr |
| H | H | CF₃ | H | —CH₂— | ![Z structure with O, N, SCH₃] | HCl |

Some of the 1,2-dihydropyridin-iminium salts of the formula (II) are known (cf. U.S. Pat. No. 3,933,836; J. Heterocycl. Chem., 12(5), 1027–1029) and/or can be prepared by processes known per se, in which 2-aminopyridine derivatives of the general formula (V)

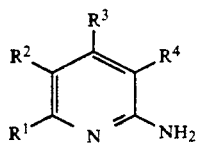

(V)

in which $R^1$, $R^2$, $R^3$ and $R^4$ have the abovementioned meanings, are reacted with compounds of the formula (VI)

X-A-Z    (VI)

in which

A and Z have the abovementioned meaning and

Z represents halogen, preferably chlorine or bromine, if appropriate in the presence of a diluent such as, for example, acetonitrile, at temperatures between 0° C. and 140° C.

2-Aminopyridine derivatives of the formula (V) and compounds of the formula (VI) are generally known compounds of organic chemistry.

Formula (III) provides a general definition of the halogen compounds furthermore to be used as starting substances in process (a) according to the invention for the preparation of compounds of the formula (I).

In formula (III), $R^{5-1}$ preferably represents straight-chain or branched alkylcarbonyl having 1 to 20 carbon atoms in the alkyl moiety, or represents in each case straight-chain or branched alkenylcarbonyl or alkynylcarbonyl each of which has 2 to 20 carbon atoms in the alkenyl or alkinyl moiety, or represents straight-chain or branched halogenoalkylcarbonyl having 1 to 20 carbon atoms in the alkyl moiety and 1 to 41 identical or different halogen atoms, or represents straight-chain or branched halogenoalkenylcarbonyl having 2 to 20 carbon atoms in the alkenyl moiety and 1 to 39 identical or different halogen atoms, or represents straight-chain or branched halogenoalkynylcarbonyl having 2 to 20 carbon atoms in the alk nyl moiety and 1 to 37 identical or different halogen atoms, or represents straight-chain or branched alkoxycarbonyl having 1 to 20 carbon atoms in the alkoxy moiety, or represents straight-chain or branched alkylthiocarbonyl having 1 to 20 carbon atoms in the alkyl moiety, or phenylcarbonyl, phenoxycarbonyl, phenylmethylcarbonyl, phenylethylcarbonyl, phenylpropylcarbonyl, phenylethenylcarbonyl, furylcarbonyl, thienylcarbonyl, pyridylcarbonyl or phenoxyrethylcarbonyl, each of which is optionally monosubstituted or polysubstituted by identical or different substituents, suitable phenyl substituents in each case being: halogen, cyano, nitro, straight-chain or branched alkyl having 1 to 4 carbon atoms, straight-chain or branched halogenoalkyl having 1 to 4 carbon atoms and 1 to 9 identical or different halogen atoms, straight-chain or branched alkoxy having 1 to 4 carbon atoms and also straight-chain or branched halogenoalkoxy having 1 to 4 carbon atoms and 1 to 9 identical or different halogen atoms; furthermore represents straight-chain or branched alkylsulphonyl having 1 to 4 carbon atoms, or represents phenylsulphonyl which is optionally monosubstituted or polysubstituted by identical or different substituents, suitable phenyl substituents being: halogen, cyano, nitro, straight-chain or branched alkyl having 1 to 4 carbon atoms, straight-chain or branched halogenoalkyl having 1 to 4 carbon atoms and 1 to 9 identical or different halogen atoms, straight-chain or branched alkoxy having 1 to 4 carbon atoms, straight-chain or branched halogenoalkoxy having 1 to 4 carbon atoms and 1 to 9 identical or different halogen atoms, and also alkoxycarbonyl having 1 to 4 carbon atoms in the straight-chain or branched alkoxy moiety, or represents cycloalkylcarbonyl having 3 to 6 carbon atoms in the cycloalkyl moiety, or represents straight-chain or alkoxyalkylcarbonyl having in each case 1 to 4 carbon atoms in the alkoxy- and alkyl moiety, or represents in each case straight-chain or branched alkylcarbonyloxyalkylcarbonyl or alkoxycarbonylcarbonyl having 1 to 4 carbon atoms in the alkoxy- or alkyl moiety respectively, or represents straight-chain or branched halogenalkylsulphonyl having 1 to 4 carbon atoms and 1 to 9 identical or different halogen atoms, $R^{5-1}$ particularly preferably represents straight-chain or branched alkylcarbonyl having 2 to 10 carbon atoms in the alkyl moiety, or represents in each case straight-chain or branched alkenylcarbonyl or alkynylcarbonyl each o-f which has 2 to 10 carbon atoms in the alkenyl or alkynyl moiety, or represents straight-chain or branched halogencalkylcarbonyl having 1 to 10 ca--bon atoms and 1 to 21 fluorine and/or chlorine atoms, or represents straight-chain or branched halogenoalkenyl-carbonyl having 2 to 10 carbon atoms in the alkenyl moiety and 1 to 19 fluorine and/or chlorine atoms, straight-,chain or branched haloqeno alkynylcarbonyl having 2 to 10 carbon atoms i-n the alkynyl moiety and 1 to 17 fluorine and/or chlorine atoms, or represents straight-chain or branched alkoxycarbonyl having 1 to 10 carbon atoms in the alkoxy moiety, or represents straight-chain or branched alkylthiocarbonyl having 1 to 10 carbon atoms in the alkyl moiety, or represents phenylcarbonyl, phenoxycarbonyl, phenylmethylcarbonyl, phenylethylcarbonyl, phenylpropylcarbonyl, phenylethenylcarbonyl, furylcarbonyl, thienylcarbonyl, pyridylcarbonyl or phenoxymethylcarbonyl, each of which is optionally monosubstituted or disubstituted by identical or different substituents from the series comprising fluorine, chlorine, bromo, cyano, nitro, methyl, trifluoromethyl or methoxy, or represents methylsulphonyl or ethylsulphonyl, or represents phenyisulphonyl which is optionally monosubstituted or disubstituted by identical or different substituents from the series comprising fluorine, chlorine, cyano, nitro, methyl, trifluoroinethyl, methoxycarbonyl or ethoxycarbonyl, or represents $C_3-C_6$-cycloalkylcarbonyl, methoxyacetyl, acetyloxyacetyl or trifluormethylsulphonyl, X preferably represents chlorine or bromine, particularly preferably chlorine.

Examples of the starting substances of the formula (III) which may be mentioned are: acetyl chloride, pivaloyl chloride, n-dodecanoyl chloride, acryloyl chloride, methacryloyl chloride, crotonyl chloride, vinylacetyl chloride, 9-dodecenoyl chloride, provionyl chloride, difluoroacetyl chloride, 2-chloropropionyl chloride, ethyl chloroformate, 4-chloro-benzoyl chloride, 3-nitrophenyl chloroformate, methylsulphonyl chloride, 3-ethoxycarbonyl-phenylsulphonyl chloride and—in the event that $R^{5-1}$ represents alkylcarbonyl, alkenylcarbonyl, alkynylcarbonyl, halogenoalkylcarbonyl, halogenoalkenylcarbonyl, halogenoalkynylcarbonyl or optionally substituted phenylcarbonyl. The following may be mentioned by way of example: acetic anhydride, acrylic anhydride, 3-chloroacrylic anhydride, propionic anhydride and trifluoroacetic anhydride.

Process (a) according to the invention for the preparation of the new 2-iminopyridine derivatives of the formula (I) is preferably carried out using diluents. Suitable diluents for this purpose are virtually all inert organic solvents. These preferably include aliphatic and aromatic, optionally halogenated hydrocarbons such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers such as diethyl ether and dibutyl ether, glycol dimethyl ether and diglycol dimethyl ether, tetrahydrofuran and dioxane, ketones such as acetone, methyl ethyl ketone, methyl isopropyl ketone and methyl isobutyl ketone, esters such as methyl acetate and ethyl acetate, nitriles such as, for example, acetonitrile and propionitrile, amides such as, for example, dimethylformamide, dimethylacetamide and N-methyl-pyrrolidone, and also dimethyl sulphoxide, tetramethylene sulphone and hexamethylphosphoric triamide.

Suitable bases for process (a) according to the invention are all inorganic and organic bases which can customarily be used. The following can preferably be used: alkali metal carbonates such as, for example, sodium and potassium carbonates; alkali metal hydroxides such as, for example, sodium hydroxide; alkali metal alcoholates such as, for example, sodium methylate, sodium ethylate, potassium methylate and potassium ethylate; alkali metal hydrides such as, for example, sodium hydride; lower tertiary alkylamines, cycloalkylamines and aralkylamines such as, in particular, triethylamine, and also alkali metal alkyl compounds such as, for example, n-butyllithium.

When carrying out process (a) according to the invention, the reaction temperatures can be varied within a substantial range. In general, the process is carried out at temperatures between 0° C. and +200° C., preferably at temperatures between +20° C. and +100° C.

For carrying out process (a) according to the invention, 1 to 1.5 moles, preferably 1 mole, of halogen compound of the formula (III) and 1 to 5 moles, preferably 1 to 3 moles, of base are generally employed per mole of 1,2-dihydropyridin-iminium salt of the formula (II).

Formula (IV) provides a general definition of the isocyanates to be used as starting substances in process (b) according to the invention for the preparation of compounds of the formula (I).

In formula (IV), $R^6$ preferably represents straight-chain or branched alkyl having 1 to 20 carbon atoms, or represents phenyl which is optionally monosubstituted or polysubstituted by identical or different substituents, substituents which may be mentioned being: halogen, cyano, nitro, straight-chain or branched alkyl having 1 to 4 carbon atoms, straight-chain or branched halogenoalkyl having 1 to 4 carbon atoms and 1 to 9 identical or different halogen atoms, straight-chain or branched alkoxy having 1 to 4 carbon atoms, and straight-chain or branched halogenoalkoxy having 1 to 4 carbon atoms and 1 to 9 identical or different halogen atoms.

$R^6$ particularly preferably represents straight-chain or branched alkyl having 1 to 10 carbon atoms or phenyl which is optionally monosubstituted or disubstituted by identical or different substituents from the series comprising fluorine, chlorine, cyano, nitro, methyl or trifluoromethyl.

Examples of the starting substances of the formula (IV) which may be mentioned are: methyl isocyanate, ethyl isocyanate, n-propyl isocyanate, n-butyl isocyanate, phenyl isocyanate, 2-chlorophenyl isocyanate, 2-cyanophenyl isocyanate, 2-trifluoromethyl isocyanate, 2-methoxycarbonylphenyl isocyanate, 3-nitrophenyl isocyanate, 3-methylphenyl isocyanate, 3-ethyoxycarbonylphenyl isocyanate, 4-fluorophenyl isocyanate, 4-trifluoromethylphenylisocyanate 4-nitrophenyl isocyanate and also 4-cyanophenyl isocyanate.

The isocyanates of the formula (IV) are generally known compounds of organic chemistry.

Process (b) according to the invention for the preparation of the new 2-iminopyridine derivatives of the formula (I) is preferably carried out using diluents. Suitable diluents for this purpose are virtually all inert organic solvents. These preferably include aliphatic and aromatic, optionally halogenated hydrocarbons such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers such as diethyl ether and dibutyl ether, glycol dimethyl ether and diglycol dimethyl ether, tetrahydrofuran and dioxane, ketones such as acetone, methyl ethyl ketone, methyl isopropyl ketone and methyl isobutyl ketone, esters such as methyl acetate and ethyl acetate, nitriles such as, for example, acetonitrile and propionitrile, amides such as, for example, dimethylformamide, dimethylacetamide and N-methyl-pyrrolidone, and also dimethyl sulphoxide, tetramethylene sulphone and hexamethylphosphoric triamide.

Suitable bases for process (b) according to the invention are all inorganic and organic bases which can customarily be used. The following can preferably be used: alkali metal carbonates such as, for example, sodium carbonate and potassium carbonate; alkali metal hydroxides such as, for example, sodium hydroxide; alkali metal alcoholates such as, for example, sodium methylate, potassium methylate, sodium ethylate and potassium ethylate; alkali metal hydrides such as, for example, sodium hydride; and also lower tertiary alkylamines, cycloalkylamines and aralkylamines such as, in particular, triethylamine.

When carrying out process (b) according to the invention, the reaction temperatures can be varied within a substantial range. In general, the process is carried out at temperatures between 0° C. and 200° C., preferably at temperatures between 20° C. and 120° C.

For carrying out process (b) according to the invention, 1 to 3 moles, preferably 1 to 1.5 moles, of isocyanate of the formula (IV) and 3 to 5 moles, preferably 2 to 2.5 moles, of base are generally employed per mole of 1,2-dihydropyridin-iminium salt of the formula (II).

The active compounds according to the invention of the formulae (I) or (IA) can be used as defoliants, desiccants, agents for destroying broad-leaved plants and, in particular, as weed-killers. By weeds, in the broadest sense, there are to be understood all plants which grow in locations where they are undesired. Whether the substances according to the invention act as total or selective herbicides depends essentially on the amount used.

The active compounds according to the invention of the formulae (I) or (IA) can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoeal Vicia, Nicotiana, Lycopersicon, Arachis, Brassica, Lactuca, Cucumis, Cucurbita, Trifolium, Ranunculus and Taraxacum.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds of the formulae (I) or (IA) is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, in lawns, turf, meadows and pastures and for the selective combating of weeds in annual cultures.

In this context, the active compounds according to the invention of the formulae (I) or (IA) are particularly suitable for selectively combating monocotyledon and dicotyledon weeds in monocotyledon crops, preemergence as well as post-emergence. Moreover some of the active compounds also have leaf-insecticidal and also soil-insecticidal and root-systemic characteristics.

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene, or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silica, alumina and silicates, as solid carriers for granules there are suitable: for example crushed and fractionated natural rocks such as calcite, marble, pumice, sepiolite and dolomite, as well As synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

For combating weeds, the active compounds according to the invention, as such or in the form of their formulations, can also be used as mixtures with known herbicides, finished formulations or tank mixes being possible.

Suitable herbicides for the mixtures are known herbicides such as, for example, 1-amino-6-ethylthio-3-(2,2-dimethylpropyl)-1,3,5-triazine-2,4(1H,3H)-dione (AMETHYDIONE) or N-(2-benzothiazolyl)-N,N'-dimethylurea (METABENZTHIAZURON) for combating weeds in cereals; 4-amino-3-methyl-6-phenyl-1,2,4-triazin-5(4H)-one (METAMITRON) for combating weeds in sugarbeets and 4-amino-6-(1,1-dimethylethyl)-3-methylthio-1,2,4-triazin-5 (4H) -one (METRIBUZIN) for combating weeds in soy beans. Mixtures with 2,4-dichlorophenoxyacetic acid (2,4-D); 4-(2,4-dichlorophenoxy)-butric acid (2,4-DB); 2,4-dichlorophenoxypropionic acid (2,4-DP); 2-chloro-2',6'-diethyl-N-methoxy-methylacetanilide (ALACHLOR); 2-chloro-4-ethylamino-6-isopropylamino-1,3,5-triazine (ATRAZINE); 3-isopropyl-2,1,3-benzothiadiazin-4-one 2,2-dioxide (BENTAZONE); methyl 5-(2,4-dichlorophenoxy)-2-nitrobenzoate (BIFENOX); 3,5-dibromo-4-hydroxy-benzonitril (BROMOXYNIL); 2-chloro-N-{[(4-methoxy-6-methyl-1,3,5-triazin-2-yl)-amino]-carbonyl}-benzenesulphonamide (CHLORSULFURON); N,N-dimethyl-N'-(3-chloro-4-methylphenyl)-urea (CHLORTOLURON); exo-1-methyl-4-(1-methylethyl)-2-(2-methylphenyl-methoxy)-7-oxabicyclo-(2,2,1)heptane (CINMETHYLIN); 3,6-dichloro-2-pyridinecarboxylic acid (CLOPYRALID); 2-chloro-4-ethylamino-6-(3-cyanopropylamino)-1,3,5-triazine (CYANAZINE); 2-[4-(2,4-dichlorophenoxy)-phenoxy]-propionic acid, its methyl ester or its ethyl ester (DICLOFOP-METHYL); S-ethyl N,N-di-n-propylthiocarbamidate (EPTAME); 4-amino-6-t-butyl-3-ethylthio-1,2,4-triazin-5(4H)-one (ETHIOZIN); 2-(4-[(6-chloro-2-benzoxazolyl)-oxy)-phenoxyl-propanoic acid, its methyl ester or its ethyl ester (FENOXAPROP); 1-methyl-3-phenyl-5-(3-trifluoromethylphenyl)-4-pyridone (FLURIDONE); [(4-amino-3,5-dichloro-6-fluoro-2-pyridinyl)-oxy]-acetic acid or its 1-methylheptyl ester (FLUROXYPYR); 3-cyclohexyl-6-dimethylamino-1-methyl-1,3,5-triazine-2,4-dione (HEXAZINONE); methyl 2-[4,5-dihydro-4-methyl-4-(1-methylethyl)-5-oxo-1H-imidazol-2-yl]-4(5)-methylbenzoate (IMAZAMETHABENZ); 3,5-diiodo-4-hydroxybenzonitrile (IOXYNIL); N,N-dimethyl-N'-(4-isopropylphenyl)-urea (ISOPROTURON); (2-methyl-4-chlorophenoxy)-acetic acid (MCPA); (4-chloro-2-methylphenoxy)-propionic acid (KCPP); N-methyl-2-(1,3-benzothiazol-2-yloxy)-acetanilide (MEFENACET); 2-chloro-N-(2,6-dimethylphenyl)-N-[(1H)-pyrazol-1-yl-methyl]-acetamide (METAZACHLOR); 2-ethyl-6-methyl-N-(l-methyl-2-methoxyethyl)-chloroacetanilide (METOLACHLOR); 2-{[[((4-methoxy-6-methyl-1,3,5-triazin-2-yl)-amino)-carbonyl]-amino]-sulphonyl}-benzoic acid or its methyl ester (METSULFURON); 2-chloro-4-trifluoromethylphenyl 3-ethoxy-4-nitro-phenyl ether (OXYFLUORFEN); N-(1-ethylpropyl)-3,4-dimethyl-2,6-dinitroaniline (PENDIMETHALIN); 2-chloro-N-isopropylacetanilide (PROPACHLOR); 0-(6-chloro-3-phenyl-pyridazin-4-yl) S-octyl thiocarbonate (PYRIDATE); 2-chloro-4,6-bis-(ethylamino)-1,3,5-triazine (SIMAZINE); 2,4-bis-[N-ethylamino]-6-methylthio-1,3,5-triazine (SIMETRYNE); 4-ethylamino-2-t-butylamino-6-methylthio-s-triazine (TERBUTRYNE); methyl 3-[[[[(4-methoxy-6-methyl-1,3,5-triazin-2-yl)-amino]carbonyl]-amino]-sulphonyl]-thiophene-2-carboxylate (THIAMETURON); S-(2,3,3-trichloroallyl) diisopropylthiocarbamate (TRIALLATE) and 2,6-dinitro-4-trifluoromethylN,N-dipropylaniline (TRIFLURALIN) are also possible. Surprisingly, some mixtures also show a synergistic action.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in a customary manner, for example by watering, spraying, atomizing or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.001 and 10 kg of active compound per hectare of soil surface, preferably between 0.005 and 5 kg per ha.

The preparation and use of the active compounds according to the invention can be seen from the following examples.

PREPARATION EXAMPLES

Example 1

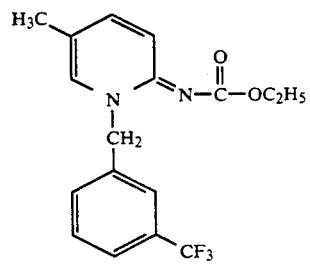

(Process (a))

3.0 g (0.01 mol) of N-[(3-trifluoromethyl)benzyl]-5-methyl-2-iminopyridine hydrochloride are dissolved in 100 ml of acetonitrile, and 2 ml of triethylamine (0.027 mol) and 1.1 g (0.01 mol) of ethyl chloroformate are added. The mixture is stirred for 18 hours at room temperature and subsequently highly concentrated. The oily residue is shaken with chloroform and water. The organic phase is separated off and crystallized by trituration with methylcyclohexane. This gives 0.7 g (21% of theory) of 2-ethoxycarbonylimino-5-methyl-1-(3-trifluoromethyl-benzyl )-1,2-dihydropyridine of melting point 121° C.

Example 2

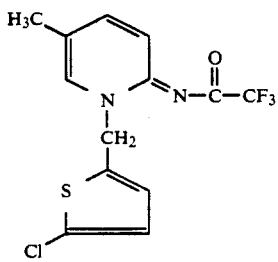

(Process (a))

1.4 g (0.005 mol) of- N- (5-chlorothien-2-yl-methyl)-5-methyl-2-iminopyridine hydrochloride are dissolved in 50 ml of acetonitrile, and 1 ml (0.013 mol) of triethylamine and 1.1 g (0.005 mol) of trifluoroacetic anhydride are added. The mixture is stirred for 18 hours at room temperature and subsequently refluxed for 4 hours. The reaction mixture is highly concentrated, the concentrate is taken up in chloroform, and the mixture is dried over sodium sulphate. After the mixture has been filtered and the solvent has been removed by distillation, the resulting residue is crystallized by trituration with methylcyclohexane. This gives 1.5 g (90% of theory) 1-(5-chlorothien-2-yl-methyl)-5-methyl-2-trifluoromethylcarbonylimino-1,2-dihydropyridine of melting point 170° C.

The compounds of the formulae (I) or (IA) according to the invention, which are listed in Table 2, can be prepared analogously to Examples 1 and 2 and following the general instructions for processes (a) and (b) according to the invention.

TABLE 2

| Ex. No. | $R^1$ | $R^2$ | $R^3$ | $R^4$ | $R^5$ or $R^{5'}$ | A | Z | Melting point or $^1$H-NMR* |
|---|---|---|---|---|---|---|---|---|
| 3 | H | —CH₃ | H | H | —C(O)—CF₃ | —CH₂— | phenyl | δ = 5.59 |
| 4 | H | —CH₃ | H | H | —C(O)—CF₃ | —CH₂— | phenyl | δ = 5.56 |
| 5 | H | H | H | H | —C(O)—CF₃ | —CH₂— | 2-Cl-phenyl | 90° C. |
| 6 | H | H | H | H | —C(O)—CF₃ | —CH₂— | 2-Cl-phenyl | δ = 5.53 |

TABLE 2-continued

| Ex. No. | R¹ | R² | R³ | R⁴ | R⁵ or R⁵' | A | Z | Melting point or ¹H-NMR* |
|---|---|---|---|---|---|---|---|---|
| 7 | H | H | H | H | —SO₂—CH₃ | —CH₂— | 2-Cl-phenyl | δ = 5.49 |
| 8 | H | H | H | H | —C(O)—OC₂H₅ | —CH₂— | 2-Cl-phenyl | δ = 5.48 (DMSO) |
| 9 | H | —CH₃ | H | H | —C(O)—CF₃ | —CH₂— | 2-Cl-phenyl | 140° C. |
| 10 | H | —CH₃ | H | H | —C(O)—CH₃ | —CH₂— | 2-Cl-phenyl | 98° C. |
| 11 | H | —CH₃ | H | H | —C(O)—CF₃ | —CH₂— | 2-NO₂-phenyl | 168° C. |
| 12 | H | —CH₃ | H | H | —C(O)—CH₃ | —CH₂— | 2-NO₂-phenyl | 157° C. |
| 13 | H | —CH₃ | H | H | —C(O)—CF₃ | —CH₂— | 3-F-phenyl | δ = 5.55 |
| 14 | H | —CH₃ | H | H | —C(O)—CCl₃ | —CH₂— | 3-F-phenyl | 153° C. |
| 15 | H | —CH₃ | H | H | —C(O)—CF₃ | —CH₂— | 3-CF₃-phenyl | 129° C. |

TABLE 2-continued
(I)
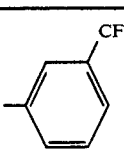
(IA)
| Ex. No. | R¹ | R² | R³ | R⁴ | R⁵ or R⁵' | A | Z | Melting point or ¹H-NMR* |
|---|---|---|---|---|---|---|---|---|
| 16 | H | —CH₃ | H | H |  | —CH₂— | 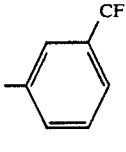 m-CF₃-C₆H₄ | $\delta = 5.44$ |
| 17 | H | —CH₃ | H | H | 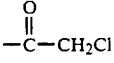 —C(O)—CCl₃ | —CH₂— | m-CF₃-C₆H₄ | 198° C. |
| 18 | H | —CH₃ | H | H | 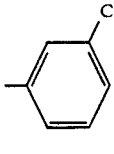 —C(O)—CH₂Cl | —CH₂— | m-CF₃-C₆H₄ | $\delta = 5.54$ |
| 19 | H | —CH₃ | H | H | 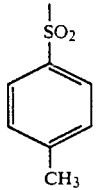 p-tolyl-SO₂— | —CH₂— | m-CF₃-C₆H₄ | $\delta = 5.37$ |
| 20 | H | —CH₃ | H | H | 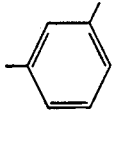 C₆H₅-SO₂— | —CH₂— | m-CF₃-C₆H₄ | $\delta = 5.37$ |
| 21 | H | —CH₃ | H | H | 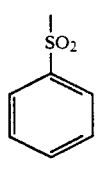 2-CF₃-C₆H₄-C(O)— | —CH₂— | m-CF₃-C₆H₄ | 148° C. |
| 22 | H | —CH₃ | H | H | 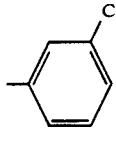 3-CF₃-C₆H₄-C(O)— | —CH₂— | m-CF₃-C₆H₄ | 134° C. |

TABLE 2-continued

|   |   |   |   |   | R⁵ or |   |   | Melting point or |
|---|---|---|---|---|---|---|---|---|
| Ex. No. | R¹ | R² | R³ | R⁴ | R⁵' | A | Z | ¹H-NMR* |
| 23 | H | —CH₃ | H | H | ethyl 2-(sulfonyl)benzoate group (H₅C₂O—O=C—C₆H₄—SO₂—) | —CH₂— | 3-CF₃-C₆H₄— | δ = 5.98 |
| 24 | H | —CH₃ | H | H | —CN | —CH₂— | 3-CF₃-C₆H₄— | 168° C. |
| 25 | H | —CH₃ | H | H | —C(O)—C₂H₅ | —CH₂— | 3-CF₃-C₆H₄— | δ = 5.50 |
| 26 | H | —CH₃ | H | H | —C(=O)—C₆H₅ | —CH₂— | 3-CF₃-C₆H₄— | δ = 5.67 |
| 27 | H | —CH₃ | H | H | —C(O)—CH(CH₃)₂ | —CH₂— | 3-CF₃-C₆H₄— | δ = 5.44 |
| 28 | H | —CH₃ | H | H | —C(=O)—C(CH₃)₃ | —CH₂— | 3-CF₃-C₆H₄— | 109° C. |
| 29 | H | H | H | H | —C(O)—CF₃ | —CH₂— | 3-CF₃-C₆H₄— | 125° C. |
| 30 | H | H | H | H | —C(O)—CH₃ | —CH₂— | 3-CF₃-C₆H₄— | 92° C. |

TABLE 2-continued

Structures (I) and (IA) with substituents $R^1, R^2, R^3, R^4$ on pyridine ring, $N-R^5$ or $N-R^{5-2}$, and $N-A-Z$.

| Ex. No. | $R^1$ | $R^2$ | $R^3$ | $R^4$ | $R^5$ or $R^{5'}$ | A | Z | Melting point or $^1$H-NMR* |
|---|---|---|---|---|---|---|---|---|
| 31 | H | H | H | H | —C(O)—CCl$_3$ | —CH$_2$— | 3-CF$_3$-phenyl | 95° C. |
| 32 | H | H | H | H | —CN | —CH$_2$— | 3-CF$_3$-phenyl | 152° C. |
| 33 | H | Cl | H | H | —C(O)—CF$_3$ | —CH$_2$— | 3-CF$_3$-phenyl | 134° C. |
| 34 | H | Cl | H | H | —C(O)—CH$_3$ | —CH$_2$— | 3-CF$_3$-phenyl | 128° C. |
| 35 | H | Cl | H | H | —C(O)—CCl$_3$ | —CH$_2$— | 3-CF$_3$-phenyl | δ = 5.65 (DMSO) |
| 36 | H | H | —CH$_3$ | H | —C(O)—CF$_3$ | —CH$_2$— | 3-CF$_3$-phenyl | 132° C. |
| 37 | H | H | —CH$_3$ | H | —C(O)—CCl$_3$ | —CH$_2$— | 3-CF$_3$-phenyl | 158° C. |
| 38 | H | H | —CH$_3$ | H | —C(O)—CH$_3$ | —CH$_2$— | 3-CF$_3$-phenyl | δ = 5.47 (DMSO) |
| 39 | H | H | H | H | —C(O)—C$_2$H$_5$ | —CH$_2$— | 3-CF$_3$-phenyl | 121° C. |

TABLE 2-continued

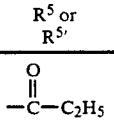

| Ex. No. | R¹ | R² | R³ | R⁴ | R⁵ or R⁵' | A | Z | Melting point or ¹H-NMR* |
|---|---|---|---|---|---|---|---|---|
| 40 | H | Cl | H | H | $-\overset{O}{\underset{\|}{C}}-C_2H_5$ | $-CH_2-$ | 3-CF₃-phenyl | 100° C. |
| 41 | H | $-CH_3$ | H | H | $\underset{C_3H_7\text{-}n}{\overset{\|}{C}=O}$ | $-CH_2-$ | 3-CF₃-phenyl | 117° C. |
| 42 | H | $-CH_3$ | H | H | $\underset{C_4H_9\text{-}n}{\overset{\|}{C}=O}$ | $-CH_2-$ | 3-CF₃-phenyl | 78° C. |
| 43 | H | $-CH_3$ | H | H | $\underset{C_4H_9\text{-}iso}{\overset{\|}{C}=O}$ | $-CH_2-$ | 3-CF₃-phenyl | 95° C. |
| 44 | H | H | H | H | $-\overset{O}{\underset{\|}{C}}-C_2H_5$ | $-CH_2-$ | 3-CF₃-phenyl | 84° C. |
| 45 | H | $-CH_3$ | H | H | $\underset{CHBr-CH_3}{\overset{\|}{C}=O}$ | $-CH_2-$ | 3-CF₃-phenyl | 85° C. |
| 46 | H | H | $-CH_3$ | H | $-\overset{O}{\underset{\|}{C}}-C_2H_5$ | $-CH_2-$ | 3-CF₃-phenyl | 152° C. |
| 47 | H | Cl | H | H | $\underset{C(CH_3)_3}{\overset{\|}{C}=O}$ | $-CH_2-$ | 3-CF₃-phenyl | 92° C. |
| 48 | H | H | H | H | $\underset{C(CH_3)_3}{\overset{\|}{C}=O}$ | $-CH_2-$ | 3-CF₃-phenyl | 138° C. |

TABLE 2-continued $$\underset{(I)}{\overset{R^3}{\underset{R^1}{\overset{R^2}{\bigcirc}}}\overset{R^4}{\underset{N}{\bigvee}}\underset{Z}{\overset{N-R^5}{\underset{A}{\mid}}}} \quad \text{or} \quad \underset{(IA)}{\overset{R^3}{\underset{R^1}{\overset{R^2}{\bigcirc}}}\overset{R^4}{\underset{N}{\bigvee}}\underset{Z}{\overset{N-R^{5-2}}{\underset{A}{\mid}}}}$$

| Ex. No. | R¹ | R² | R³ | R⁴ | R⁵ or R⁵' | A | Z | Melting point or ¹H-NMR* |
|---|---|---|---|---|---|---|---|---|
| 49 | H | H | H | H | $-\overset{O}{\underset{}{C}}-CH(CH_3)_2$ | $-CH_2-$ | 3-CF₃-C₆H₄ | 98° C. |
| 50 | H | $-CH_3$ | H | H | $-\overset{O}{\underset{}{C}}-CF_3$ | $-CH_2-$ | 3-OCH₃-C₆H₄ | δ = 5.53 |
| 51 | H | $-CH_3$ | H | H | $-\overset{O}{\underset{}{C}}-CH_3$ | $-CH_2-$ | 3-OCH₃-C₆H₄ | δ = 5.49 |
| 52 | H | $-CH_3$ | H | H | $-\overset{O}{\underset{}{C}}-CCl_3$ | $-CH_2-$ | 3-OCH₃-C₆H₄ | δ = 5.59 |
| 53 | H | $-CH_3$ | H | H | $-\overset{O}{\underset{}{C}}-CH_3$ | $-CH_2-$ | 3-CH₃-C₆H₄ | δ = 5.42 |
| 54 | H | $-CH_3$ | H | H | $-\overset{O}{\underset{}{C}}-CF_3$ | $-CH_2-$ | 4-F-C₆H₄ | δ = 5.52 |
| 55 | H | $-CH_3$ | H | H | $-\overset{O}{\underset{}{C}}-CH_3$ | $-CH_2-$ | 4-F-C₆H₄ | 130° C. |
| 56 | H | $-CH_3$ | H | H | $-\overset{O}{\underset{}{C}}-CCl_3$ | $-CH_2-$ | 4-F-C₆H₄ | δ = 5.58 |
| 57 | H | $-CH_3$ | H | H | $-\overset{O}{\underset{}{C}}-CH_2Cl$ | $-CH_2-$ | 4-F-C₆H₄ | δ = 5.50 |
| 58 | H | $-CH_3$ | H | H | $-CN$ | $-CH_2-$ | 4-F-C₆H₄ | 226° C. |

TABLE 2-continued

Structures (I) and (IA):

Pyridine ring with substituents R² (position 5), R³ (position 4), R⁴ (position 3), R¹ (position 6), N-A-Z at position 1, and =N-R⁵ (or =N-R⁵') at position 2.

| Ex. No. | R¹ | R² | R³ | R⁴ | R⁵ or R⁵' | A | Z | Melting point or ¹H-NMR* |
|---|---|---|---|---|---|---|---|---|
| 59 | H | H | H | H | -C(=O)-CF₃ | -CH₂- | 4-F-C₆H₄ | 138° C. |
| 60 | H | H | H | H | -C(=O)-CH₃ | -CH₂- | 4-F-C₆H₄ | 93° C. |
| 61 | H | H | H | H | -C(=O)-CCl₃ | -CH₂- | 4-F-C₆H₄ | δ = 5.58 |
| 62 | H | Cl | H | H | -C(=O)-CF₃ | -CH₂- | 4-F-C₆H₄ | 149° C. |
| 63 | H | Cl | H | H | -C(=O)-CH₃ | -CH₂- | 4-F-C₆H₄ | δ = 5.35 |
| 64 | H | Cl | H | H | -C(=O)-CCl₃ | -CH₂- | 4-F-C₆H₄ | 190° C. |
| 65 | H | -CH₃ | H | H | -C(=O)-C₂H₅ | -CH₂- | 4-F-C₆H₄ | 132° C. |
| 66 | H | -CH₃ | H | H | -C(=O)-C(CH₃)₃ | -CH₂- | 4-F-C₆H₄ | 90° C. |
| 67 | H | -CH₃ | H | H | -C(=O)-CF₃ | -CH₂- | 4-CF₃-C₆H₄ | 107° C. |
| 68 | H | -CH₃ | H | H | -C(=O)-CCl₃ | -CH₂- | 4-CF₃-C₆H₄ | 143° C. |
| 69 | H | -CH₃ | H | H | -C(=O)-CH₃ | -CH₂- | 4-CF₃-C₆H₄ | 135° C. |

TABLE 2-continued $$\text{(I)} \quad \text{or} \quad \text{(IA)}$$

| Ex. No. | R¹ | R² | R³ | R⁴ | R⁵ or R⁵′ | A | Z | Melting point or ¹H-NMR* |
|---|---|---|---|---|---|---|---|---|
| 70 | H | —CH₃ | H | H | —C(=O)—CF₃ | —CH₂— | 2-CF₃-C₆H₄ | 149° C. |
| 71 | H | —CH₃ | H | H | —C(=O)—CF₃ | —CH₂— | 3-Cl-C₆H₄ | 131° C. |
| 72 | H | —CH₃ | H | H | —C(=O)—CH₃ | —CH₂— | 3-Cl-C₆H₄ | 88° C. |
| 73 | H | —CH₃ | H | H | —C(=O)—CCl₃ | —CH₂— | 3-Cl-C₆H₄ | δ = 5.56 |
| 74 | H | H | H | H | —C(=O)—CF₃ | —CH₂— | 3-Cl-C₆H₄ | 140° C. |
| 75 | H | H | H | H | —C(=O)—CH₃ | —CH₂— | 3-Cl-C₆H₄ | 92° C. |
| 76 | H | H | H | H | —C(=O)—CCl₃ | —CH₂— | 3-Cl-C₆H₄ | 140° C. |
| 77 | H | Cl | H | H | —C(=O)—CF₃ | —CH₂— | 3-Cl-C₆H₄ | 152° C. |
| 78 | H | Cl | H | H | —C(=O)—CCl₃ | —CH₂— | 3-Cl-C₆H₄ | 185° C. |

TABLE 2-continued

| Ex. No. | $R^1$ | $R^2$ | $R^3$ | $R^4$ | $R^5$ or $R^{5'}$ | A | Z | Melting point or $^1$H-NMR* |
|---|---|---|---|---|---|---|---|---|
| 79 | H | —CH$_3$ | H | H | —C(O)—C$_2$H$_5$ | —CH$_2$— | 3-Cl-phenyl | 114° C. |
| 80 | H | —CH$_3$ | H | H | —C(=O)—C(CH$_3$)$_3$ | —CH$_2$— | 3-Cl-phenyl | 141° C. |
| 81 | H | Cl | H | H | —C(O)—C$_2$H$_5$ | —CH$_2$— | 3-Cl-phenyl | 111° C. |
| 82 | H | Cl | H | H | —C(O)—CH$_3$ | —CH$_2$— | 3-Cl-phenyl | δ = 5.33 |
| 83 | H | CH$_3$ | H | H | —C(=O)—CH(CH$_3$)$_2$ | —CH$_2$— | 3-Cl-phenyl | 110° C. |
| 84 | H | —CH$_3$ | H | H | —C(O)—CF$_3$ | —CH$_2$— | 2,4-diCl-phenyl | 125° C. |
| 85 | H | —CH$_3$ | H | H | —C(O)—CH$_3$ | —CH$_2$— | 2,4-diCl-phenyl | 136° C. |
| 86 | H | —CH$_3$ | H | H | —SO$_2$CH$_3$ | —CH$_2$— | 2,4-diCl-phenyl | 176° C. |
| 87 | H | —CH$_3$ | H | H | —C(=O)—OC$_2$H$_5$ | —CH$_2$— | 2,4-diCl-phenyl | 165° C. |

TABLE 2-continued

Structures (I) and (IA): pyridine ring with substituents R¹ (position 6, adjacent to N), R² (position 5), R³ (position 4), R⁴ (position 3), and =N-R⁵ or =N-R⁵⁻² at position 2; N bears -A-Z.

| Ex. No. | R¹ | R² | R³ | R⁴ | R⁵ or R⁵' | A | Z | Melting point or ¹H-NMR* |
|---|---|---|---|---|---|---|---|---|
| 88 | H | —CH₃ | H | H | 4-methylphenyl-SO₂— | —CH₂— | 2,4-dichlorophenyl | 168° C. |
| 89 | H | —CH₃ | H | H | phenyl-SO₂— | —CH₂— | 2,4-dichlorophenyl | 169° C. |
| 90 | H | —CH₃ | H | H | 2-(ethoxycarbonyl)phenyl-SO₂— (H₅C₂O-C(=O)-C₆H₄-SO₂—) | —CH₂— | 2,4-dichlorophenyl | 152° C. |
| 91 | H | Cl | H | H | —C(=O)—CF₃ | —CH₂— | 2,4-dichlorophenyl | 124° C. |
| 92 | H | Cl | H | H | —C(=O)—CH₃ | —CH₂— | 2,4-dichlorophenyl | 135° C. |
| 93 | H | H | H | H | —C(=O)—CF₃ | —CH₂— | 2,4-dichlorophenyl | δ = 5.68 (DMSO) |
| 94 | H | —CH₃ | H | H | —C(=O)—CF₃ | —CH₂— | 2,4-difluorophenyl | 149° C. |

TABLE 2-continued

Structures (I) and (IA): pyridine ring with substituents R$^1$ (position 6), R$^2$ (position 5), R$^3$ (position 4), R$^4$ (position 3), =N—R$^5$ or =N—R$^{5'}$ (position 2), and N—A—Z (position 1).

| Ex. No. | R$^1$ | R$^2$ | R$^3$ | R$^4$ | R$^5$ or R$^{5'}$ | A | Z | Melting point or $^1$H-NMR* |
|---|---|---|---|---|---|---|---|---|
| 95 | H | —CH$_3$ | H | H | —C(O)—CH$_3$ | —CH$_2$— | 2,4-difluorophenyl | δ = 5.37 |
| 96 | H | —CH$_3$ | H | H | —C(O)—CF$_3$ | —CH$_2$— | 3,5-bis(CF$_3$)phenyl | δ = 5.59 |
| 97 | H | —CH$_3$ | H | H | —C(O)—CF$_3$ | —CH$_2$— | 3,4-dichlorophenyl | 160° C. |
| 98 | H | —CH$_3$ | H | H | —C(O)—CH$_3$ | —CH$_2$— | 3,4-dichlorophenyl | 142° C. |
| 99 | H | —CH$_3$ | H | H | —C(O)—CH$_3$ | —CH$_2$— | 2-CF$_3$-4-Cl-phenyl | 140° C. |
| 100 | H | —CH$_3$ | H | H | —C(O)—CH$_3$ | —CH$_2$— | 3-CF$_3$-4-Cl-phenyl | 150° C. |
| 101 | H | —CH$_3$ | H | H | —C(O)—CF$_3$ | —CH$_2$— | 3-CF$_3$-4-Cl-phenyl | 138° C. |
| 102 | H | —CH$_3$ | H | H | —C(O)—CF$_3$ | —CH$_2$— | 2-Cl-3-CF$_3$-phenyl | 154° C. |

TABLE 2-continued

| | | | | | R⁵ or | | | Melting point or |
|---|---|---|---|---|---|---|---|---|
| Ex. No. | R¹ | R² | R³ | R⁴ | R⁵' | A | Z | ¹H-NMR* |
| 103 | H | —CH₃ | H | H | —C(O)—CH₃ | —CH₂— | 2-Cl, 3-CF₃ phenyl | 147° C. |
| 104 | H | —CH₃ | H | H | —C(O)—CF₃ | —CH₂— | 2-CF₃, 4-Cl phenyl | 104° C. |
| 105 | H | —CH₃ | H | H | —C(O)—CF₃ | —CH₂— | 2-chloro-5-methylthiazolyl | 198° C. |
| 106 | H | —CH₃ | H | H | —C(O)—CH₃ | —CH₂— | 2-chloro-5-methylthiazolyl | 183° C. |
| 107 | H | —CH₃ | H | H | —C(O)—CH₂Cl | —CH₂— | 2-chloro-5-methylthiazolyl | δ = 5.48 |
| 108 | H | —CH₃ | H | H | 2-(SO₂CH₃)-benzoate ethyl ester | —CH₂— | 2-chloro-5-methylthiazolyl | δ = 5.35 |
| 109 | H | —CH₃ | H | H | —CN | —CH₂— | 2-chloro-5-methylthiazolyl | 205° C. |
| 110 | H | H | H | H | —C(O)—CH₃ | —CH₂— | 2-chloro-5-methylthiazolyl | δ = 5.35 |
| 111 | H | H | H | H | —C(O)—CCl₃ | —CH₂— | 2-chloro-5-methylthiazolyl | 192° C. |
| 112 | H | H | H | H | —C(O)—CF₃ | —CH₂— | 2-chloro-5-methylthiazolyl | 146° C. |
| 113 | H | Cl | H | H | —C(O)—CF₃ | —CH₂— | 2-chloro-5-methylthiazolyl | 170° C. |

TABLE 2-continued

| Ex. No. | R¹ | R² | R³ | R⁴ | R⁵ or R⁵' | A | Z | Melting point or ¹H-NMR* |
|---|---|---|---|---|---|---|---|---|
| 114 | H | Cl | H | H | −CO−CH₃ | −CH₂− | 2-chloro-thiazol-5-ylmethyl | δ = 5.30 |
| 115 | H | Cl | H | H | −CO−CH₂Cl | −CH₂− | 2-chloro-thiazol-5-ylmethyl | 176° C. |
| 116 | H | Cl | H | H | −CO−CCl₃ | −CH₂− | 2-chloro-thiazol-5-ylmethyl | 169° C. |
| 117 | H | Cl | H | H | −CN | −CH₂− | 2-chloro-thiazol-5-ylmethyl | 214° C. |
| 118 | H | H | −CH₃ | H | −CO−CF₃ | −CH₂− | 2-chloro-thiazol-5-ylmethyl | δ = 5.52 |
| 119 | H | H | −CH₃ | H | −CO−CH₃ | −CH₂− | 2-chloro-thiazol-5-ylmethyl | 238° C. |
| 120 | H | H | −CH₃ | H | −SO₂−CH₃ | −CH₂− | 2-chloro-thiazol-5-ylmethyl | δ = 5.29 |
| 121 | H | H | −CH₃ | H | −CO−CCl₃ | −CH₂− | 2-chloro-thiazol-5-ylmethyl | 163° C. |
| 122 | H | H | H | −CH₃ | −CO−CF₃ | −CH₂− | 2-chloro-thiazol-5-ylmethyl | δ = 5.57 |
| 123 | H | H | H | −CH₃ | −CO−CH₃ | −CH₂− | 2-chloro-thiazol-5-ylmethyl | δ = 5.40 |
| 124 | H | H | H | −CH₃ | −SO₂−CH₃ | −CH₂− | 2-chloro-thiazol-5-ylmethyl | 160° C. |
| 125 | H | −CH₃ | H | H | −CO−C₂H₅ | −CH₂− | 2-chloro-thiazol-5-ylmethyl | 197° C. |

TABLE 2-continued

| Ex. No. | R¹ | R² | R³ | R⁴ | R⁵ or R⁵' | A | Z | Melting point or ¹H-NMR* |
|---|---|---|---|---|---|---|---|---|
| 126 | H | H | H | H | —C(=O)—C₂H₅ | —CH₂— | (5-methyl-2-chloro-thiazol-yl) | 183° C. |
| 127 | H | —CH₃ | H | H | —C(=O)—C(CH₃)₃ | —CH₂— | (5-methyl-2-chloro-thiazol-yl) | 120° C. |
| 128 | H | —CH₃ | H | H | —C(=O)—CH(CH₃)₂ | —CH₂— | (5-methyl-2-chloro-thiazol-yl) | 118° C. |
| 129 | H | Cl | H | H | —C(=O)—C(CH₃)₃ | —CH₂— | (5-methyl-2-chloro-thiazol-yl) | 107° C. |
| 130 | H | Cl | H | H | —C(=O)—CH(CH₃)₂ | —CH₂— | (5-methyl-2-chloro-thiazol-yl) | 114° C. |
| 131 | H | Cl | H | H | —C(=O)—OC₂H₅ | —CH₂— | (5-methyl-2-chloro-thiazol-yl) | 149° C. |
| 132 | H | —CH₃ | H | H | —C(=O)—NHCH₃ | —CH₂— | (3-trifluoromethylphenyl) | δ = 5.30 |
| 133 | H | —CH₃ | H | H | —C(=O)—CF₃ | —CH₂— | (2-chloropyridin-5-yl) | 140° C. |
| 134 | H | H | H | H | —C(=O)—CF₃ | —CH₂— | (3-chloro-5-methyl-isothiazol-yl) | 153° C. |
| 135 | H | —CH₃ | H | H | —C(=O)—CF₃ | —CH₂— | (3,4-dimethyl-isoxazol-5-yl) | 128° C. |
| 136 | H | H | —CH₃ | H | —C(=O)—CF₃ | —CH₂— | (3-methyl-isoxazol-5-yl) | 113° C. |

TABLE 2-continued

| Ex. No. | R¹ | R² | R³ | R⁴ | R⁵ or R⁵' | A | Z | Melting point or ¹H-NMR* |
|---|---|---|---|---|---|---|---|---|
| 137 | H | —CH₃ | H | H | —C(=O)—CF₃ | —CH₂— | 3-methyl-5-isoxazolyl | 137° C. |
| 138 | H | H | H | H | —C(=O)—CF₃ | —CH₂— | 3-methyl-5-isoxazolyl | 171° C. |
| 139 | H | —CH₃ | H | H | —C(=O)—CF₃ | —CH₂— | 3-chloro-5-isoxazolyl | 146° C. |
| 140 | H | H | —CH₃ | H | —C(=O)—CF₃ | —CH₂— | 3-chloro-5-isoxazolyl | 143° C. |
| 141 | H | H | H | H | —C(=O)—CF₃ | —CH₂— | 3-chloro-5-isoxazolyl | 170° C. |
| 142 | H | H | H | H | —C(=O)—CF₃ | —CH₂— | 3,5-dimethyl-1,2,4-oxadiazolyl | 135° C. |
| 143 | H | H | —CH₃ | H | —C(=O)—CF₃ | —CH₂— | 3,5-dimethyl-1,2,4-oxadiazolyl | 127° C. |
| 144 | H | —CH₃ | H | H | —C(=O)—CF₃ | —CH₂— | 3,5-dimethyl-1,2,4-oxadiazolyl | 154° C. |
| 145 | H | Cl | H | H | —C(=O)—CH(CH₃)₂ | —CH₂— | 2-chloro-5-methylthiazolyl | 120° C. |
| 146 | H | —CH₃ | H | H | —C(=O)—OC₂H₅ | —CH₂— | phenyl | 109° C. |
| 147 | H | —CH₃ | H | H | —C(=O)—CCl₃ | —CH₂— | phenyl | 138° C. |

TABLE 2-continued

Structures (I) and (IA) with substituents R¹, R², R³, R⁴, R⁵ or R⁵', A, and Z.

| Ex. No. | R¹ | R² | R³ | R⁴ | R⁵ or R⁵' | A | Z | Melting point or ¹H-NMR* |
|---|---|---|---|---|---|---|---|---|
| 148 | H | —CH₃ | H | H | —C(O)—CF₃ | —CH₂— | 3-NO₂-phenyl | 158° C. |
| 149 | H | —CH₃ | H | H | —C(O)—OC₂H₅ | —CH₂— | 4-F-phenyl | 104° C. |
| 150 | H | —CH₃ | H | H | —C(O)—CH₃ | —CH₂— | 3-NO₂-phenyl | 155° C. |
| 151 | H | —CH₃ | H | H | —C(O)—CH₃ | —CH₂— | 3-phenoxyphenyl | 150° C. |
| 152 | H | —CH₃ | H | H | —C(O)—CF₃ | —CH₂— | 3,5-dichlorophenyl | 186° C. |
| 153 | H | —CH₃ | H | H | —C(O)—CH₃ | —CH₂— | 3,5-dichlorophenyl | 173° C. |
| 154 | H | —CH₃ | H | H | —C(O)—C(CH₃)₃ | —CH₂— | phenyl | 80° C. |
| 155 | H | —CH₃ | H | H | —C(O)—CF₃ | —CH₂— | 3-phenoxyphenyl | 104° C. |

TABLE 2-continued
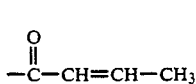
| Ex. No. | R¹ | R² | R³ | R⁴ | R⁵ or R⁵' | A | Z | Melting point or ¹H-NMR* |
|---|---|---|---|---|---|---|---|---|
| 156 | H | —CH₃ | H | H | 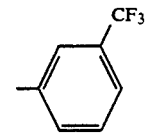 | —CH₂— |  3-CF₃-phenyl | 124° C. |
| 157 | H | —CF₃ | H | H | 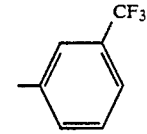 —CO—CF₃ | —CH₂— | 3-CF₃-phenyl | 108° C. |
| 158 | H | —CH₃ | H | H | 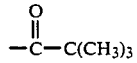 —CO—C(CH₃)₃ | —CH₂— | 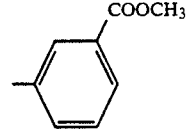 3-COOCH₃-phenyl | Öl |
| 159 | H | CH₃ | H | H | 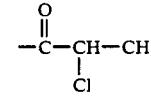 —CO—CH(Cl)—CH₃ | —CH₂— | 3-CF₃-phenyl | 80° C. |
| 160 | H | CH₃ | H | H | —SO₂—CH₃ | —CH₂— | 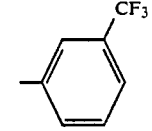 4-CF₃-phenyl | Oil |
| 161 | H | CH₃ | H | H | —CO—CHCl₂ | —CH₂— | 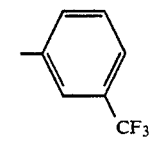 3-CF₃-phenyl | Oil |
| 162 | H | CH₃ | H | H | —CO—CF₃ | —CH₂— | 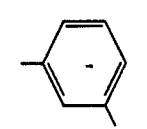 3-CH₃-phenyl | 92° C. |
| 163 | H | CH₃ | H | H | —CO—CH(CH₃)₂ | —CH₂— | 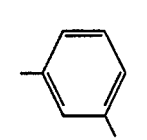 4-F-phenyl | 66° C. |

TABLE 2-continued

Structures (I) and (IA): pyridine ring with substituents R¹ (position 6), R² (position 5), R³ (position 4), R⁴ (position 3), =N—R⁵ (or =N—R⁵⁻²) at position 2, and N—A—Z at ring nitrogen.

| Ex. No. | R¹ | R² | R³ | R⁴ | R⁵ or R⁵' | A | Z | Melting point or ¹H-NMR* |
|---|---|---|---|---|---|---|---|---|
| 164 | H | Cl | H | H | —CO—CH(CH₃)₂ | —CH₂ | 3-CF₃-phenyl | 83° C. |
| 165 | H | CH₃ | H | H | —CO—cyclopropyl | —CH₂ | 3-CF₃-phenyl | 76° C. |
| 166 | H | CH₃ | H | H | —CO—(4-Cl-phenyl) | —CH₂— | 3-CF₃-phenyl | 181° C. |
| 167 | H | CH₃ | H | H | —CO—(2-chloropyridin-3-yl) | —CH₂— | 3-CF₃-phenyl | 127° C. |
| 168 | H | CH₃ | H | H | —CO—CF₃ | —CH₂— | 3-COOCH₃-phenyl | 102° C. |
| 169 | H | CH₃ | H | H | —CO—CH₂C₆H₅ | —CH₂— | 3-CF₃-phenyl | amorph |
| 170 | H | CH₃ | H | H | —COOC(CH₃)₂C₂H₅ | —CH₂— | 3-CF₃-phenyl | 105° C. |
| 171 | H | CH₃ | H | H | —CO—C₁₁H₂₃ | —CH₂— | 3-CF₃-phenyl | 52° C. |

TABLE 2-continued

Structures (I) and (IA): pyridine rings with substituents R², R³, R⁴ at ring positions, R¹ at position 6, =N—R⁵ (or =N—R⁵·) at position 2, and N—A—Z at ring nitrogen.

| Ex. No. | R¹ | R² | R³ | R⁴ | R⁵ or R⁵' | A | Z | Melting point or ¹H-NMR* |
|---|---|---|---|---|---|---|---|---|
| 172 | H | CH₃ | H | H | —COOC(CH₃)₃ | —CH₂— | 3-CF₃-phenyl | 143° C. |
| 173 | H | CH₃ | H | H | —COOCH₃ | —CH₂— | 3-CF₃-phenyl | 94° C. |
| 174 | H | CH₃ | H | H | —CO—C₅H₁₁ | —CH₂— | 3-CF₃-phenyl | 56° C. |
| 175 | H | CH₃ | H | H | —CO—C₆H₁₃ | —CH₂— | 3-CF₃-phenyl | 74° C. |
| 176 | H | CH₃ | H | H | —CO—CH(C₂H₅)(phenyl) | —CH₂— | 3-CF₃-phenyl | 135° C. |
| 177 | H | CH₃ | H | H | —CO—COOC₂H₅ | —CH₂— | 3-CF₃-phenyl | 153° C. |
| 178 | H | CH₃ | H | H | —CO—CH₂CH(CH₃)₂ | —CH₂— | 4-methyl-2-chloro-thiazol-5-yl | 112° C. |
| 179 | H | CH₃ | H | H | —CO—CHCH₃(Br) | —CH₂— | 4-methyl-2-chloro-thiazol-5-yl | 122° C. |
| 180 | H | CH₃ | H | H | —CO—C₃H₇ | —CH₂— | 4-methyl-2-chloro-thiazol-5-yl | 138° C. |

TABLE 2-continued

Structures (I) and (IA): pyridine ring with substituents $R^1$ (position 6), $R^2$ (position 5), $R^3$ (position 4), $R^4$ (position 3), ring N bearing A–Z group, and exocyclic =N–$R^5$ (I) or =N–$R^{5-2}$ (IA) at position 2.

| Ex. No. | $R^1$ | $R^2$ | $R^3$ | $R^4$ | $R^5$ or $R^{5\prime}$ | A | Z | Melting point or $^1$H-NMR* |
|---|---|---|---|---|---|---|---|---|
| 181 | H | CH$_3$ | H | H | —CO—C$_4$H$_9$ | —CH$_2$— | 4-methyl-2-chloro-thiazol-5-yl | 133° C. |
| 182 | H | CH$_3$ | H | H | —CO—CH$_2$C(CH$_3$)$_3$ | —CH$_2$— | 3-(CF$_3$)phenyl | 96° C. |
| 183 | H | CH$_3$ | H | H | —CO—C(CH$_3$)$_3$ | —CH$_2$— | 3-methylphenyl | 121° C. |
| 184 | H | CH$_3$ | H | H | —CO—CH=CHCH$_3$ | —CH$_2$— | 4-methyl-2-chloro-thiazol-5-yl | 180° C. |
| 185 | H | CH$_3$ | H | H | —CO—(3-chlorophenyl) | —CH$_2$— | 3-(CF$_3$)phenyl | 115° C. |
| 186 | H | CH$_3$ | H | H | —CO—(3-nitrophenyl) | —CH$_2$— | 3-(CF$_3$)phenyl | 149° C. |
| 187 | H | CH$_3$ | H | H | —CO—C$_2$F$_2$ | —CH$_2$— | 3-(CF$_3$)phenyl | 70° C. |
| 188 | H | CH$_3$ | H | H | —CO—(furan-2-yl) | —CH$_2$— | 3-(CF$_3$)phenyl | 144° C. |
| 189 | H | CH$_3$ | H | H | —CO—(6-chloropyridin-3-yl) | —CH$_2$— | 3-(CF$_3$)phenyl | 157° C. |

TABLE 2-continued

Structures (I) and (IA): pyridine rings with substituents $R^1$, $R^2$, $R^3$, $R^4$, N-A-Z, and =N-$R^5$ (or =N-$R^{5\cdot 2}$).

| Ex. No. | $R^1$ | $R^2$ | $R^3$ | $R^4$ | $R^5$ or $R^{5'}$ | A | Z | Melting point or $^1$H-NMR* |
|---|---|---|---|---|---|---|---|---|
| 190 | H | CH$_3$ | H | H | —CO—C$_6$H$_4$—OCH$_3$ (4-OCH$_3$) | —CH$_2$— | 3-CF$_3$-C$_6$H$_4$ | 123° C. |
| 191 | H | CH$_3$ | H | H | —CO—C$_6$H$_4$—CH$_3$ (4-CH$_3$) | —CH$_2$— | 3-CF$_3$-C$_6$H$_4$ | 138° C. |
| 192 | H | CH$_3$ | H | H | —CO—C$_6$H$_4$—Br (4-Br) | —CH$_2$— | 3-CF$_3$-C$_6$H$_4$ | 168° C. |
| 193 | H | CH$_3$ | H | H | —CO—CH$_2$OCH$_3$ | —CH$_2$— | 3-CF$_3$-C$_6$H$_4$ | 140° C. |
| 194 | H | CH$_3$ | H | H | —CO-(2-thienyl) | —CH$_2$— | 3-CF$_3$-C$_6$H$_4$ | 130° C. |
| 195 | H | CH$_3$ | H | H | —CO—CH=CHCH$_3$ | —CH$_2$— | C$_6$H$_5$ | 57° C. |
| 196 | H | CH$_3$ | H | H | —CO-(2-Cl-pyridin-3-yl) | —CH$_2$— | C$_6$H$_6$ | amorph |
| 197 | H | CH$_3$ | H | H | —COOCH$_3$ | —CH$_2$— | C$_6$H$_5$ | 72° C. |
| 198 | H | CH$_3$ | H | H | —CO—CH=CHCH$_3$ | —CH$_2$— | 3-Cl-C$_6$H$_4$ | 105° C. |
| 199 | H | CH$_3$ | H | H | —COOCH$_3$ | —CH$_2$— | 3-Cl-C$_6$H$_4$ | 95° C. |

TABLE 2-continued
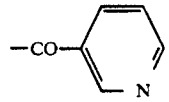
| Ex. No. | R¹ | R² | R³ | R⁴ | R⁵ or R⁵' | A | Z | Melting point or ¹H-NMR* |
|---|---|---|---|---|---|---|---|---|
| 200 | H | $CH_3$ | H | H | -CO-(3-pyridyl) | $-CH_2-$ | 3-$CF_3$-phenyl | 139° C. |
| 201 | H | $CH_3$ | H | H | -CO-(4-pyridyl) | $-CH_2-$ | 3-$CF_3$-phenyl | 190° C. |
| 202 | H | $CH_3$ | H | H | $-CO-CF_3$ | $-CH_2-$ | 3-Br-phenyl | 122° C. |
| 203 | H | $CH_3$ | H | H | $-COOC_2H_5$ | $-CH_2-$ | 3-Br-phenyl | 59° C. |
| 204 | H | $CH_3$ | H | H | $-CO-C(CH_3)_3$ | $-CH_2-$ | 3-Br-phenyl | 113° C. |
| 205 | H | $CH_3$ | H | H | -CO-(2-Cl-3-pyridyl) | $-CH_2-$ | 3-Br-phenyl | 155° C. |
| 206 | H | $CH_3$ | H | H | $-CO-CF_3$ | $-CH_2-$ | 3-CN-phenyl | 129° C. |
| 207 | H | $CH_3$ | H | H | $-CO-C(CH_3)_3$ | $-CH_2-$ | 3-CN-phenyl | 96° C. |

TABLE 2-continued

Structure (I): pyridine ring with R³ (4-position), R² (5-position), R⁴ (3-position), R¹ (6-position), N (1-position) bearing A-Z, and =N-R⁵ at 2-position.

Structure (IA): same as (I) but with =N-R⁵⁻² at 2-position.

| Ex. No. | R¹ | R² | R³ | R⁴ | R⁵ or R⁵' | A | Z | Melting point or ¹H-NMR* |
|---|---|---|---|---|---|---|---|---|
| 208 | H | CH₃ | H | H | —COOC₂H₅ | —CH₂— | 3-CN-phenyl | 116° C. |
| 209 | H | CH₃ | H | H | —CO—(2-chloropyridin-3-yl) | —CH₂— | 3-CN-phenyl | 144° C. |
| 210 | H | CH₃ | H | H | —CO—C₂H₅ | —CH₂— | 3-NO₂-phenyl | 128° C. |
| 211 | H | CH₃ | H | H | —CO—C₃H₇ | —CH₂— | 3-NO₂-phenyl | 104° C. |
| 212 | H | CH₃ | H | H | —CO—CH(CH₃)₂ | —CH₂— | 3-NO₂-phenyl | 80° C. |
| 213 | H | CH₃ | H | H | —CO—CH=CHCH₃ | —CH₂— | 3-NO₂-phenyl | 132° C. |
| 214 | H | CH₃ | H | H | —CO—C₄H₉ | —CH₂— | 3-NO₂-phenyl | 94° C. |
| 215 | H | CH₃ | H | H | —CO—CH₂CH(CH₃)₂ | —CH₂— | 4-NO₂-phenyl | 96° C. |

TABLE 2-continued
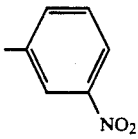
| Ex. No. | R¹ | R² | R³ | R⁴ | R⁵ or R⁵′ | A | Z | Melting point or ¹H-NMR* |
|---|---|---|---|---|---|---|---|---|
| 216 | H | CH₃ | H | H | —CO—C(CH₃)₃ | —CH₂— | 3-NO₂-C₆H₄ | 98° C. |
| 217 | H | CH₃ | H | H | —COOCH₃ | —CH₂— | 3-NO₂-C₆H₄ | 141° C. |
| 218 | H | CH₃ | H | H | —COOC₂H₅ | —CH₂— | 3-NO₂-C₆H₄ | 131° C. |
| 219 | H | CH₃ | H | H | —CO—C₆H₅ | —CH₂— | 3-NO₂-C₆H₄ | 137° C. |
| 220 | H | CH₃ | H | H | —COOC₂H₅ | —CH₂— | 3-Cl-C₆H₄ | 71° C. |
| 221 | H | CH₃ | H | H | —CO—CH=CHC₆H₅ | —CH₂— | 3-CF₃-C₆H₄ | 118° C. |
| 222 | H | Cl | H | H | —CO—CF₃ | —CH₂— | 3-NO₂-C₆H₄ | 136° C. |
| 223 | H | CH₃ | H | H | —CO—CF₃ | —CH₂— | 2-H₃CO-4-NO₂-C₆H₃ | 196° C. |

TABLE 2-continued

Structures (I) and (IA) shown with substituents R¹, R², R³, R⁴, R⁵ or R⁵', A, Z.

| Ex. No. | R¹ | R² | R³ | R⁴ | R⁵ or R⁵' | A | Z | Melting point or ¹H-NMR* |
|---|---|---|---|---|---|---|---|---|
| 224 | H | CH₃ | H | H | —CO—C(CH₃)₃ | —CH₂— | 2-OCH₃, 4-NO₂-phenyl | 189° C. |
| 225 | H | CH₃ | H | H | —CO—CF₃ | —CH₂— | 2-Cl, 4-NO₂-phenyl | 140° C. |
| 226 | H | CH₃ | H | H | —CO—C(CH₃)₃ | —CH₂— | 2-Cl, 4-NO₂-phenyl | 162° C. |
| 227 | H | CH₃ | H | H | —CO—CH₂OCH₃ | —CH₂— | 3-NO₂-phenyl | 150° C. |
| 228 | H | CH₃ | H | H | —CO—CH₂OC₆H₅ | —CH₂— | 3-CF₃-phenyl | 113° C. |
| 229 | H | CH₃ | H | H | —CO—CH₂O—(4-Cl-phenyl) | —CH₂— | 3-CF₃-phenyl | 96° C. |
| 230 | H | CH₃ | H | H | —CO—CH₂OCOCH₃ | —CH₂— | 3-CF₃-phenyl | 84° C. |
| 231 | H | CH₃ | H | H | —CO—C(Cl)=CCl₂ | —CH₂— | 3-CF₃-phenyl | 102° C. |

TABLE 2-continued

| Ex. No. | R¹ | R² | R³ | R⁴ | R⁵ or R⁵' | A | Z | Melting point or $^1$H-NMR* |
|---|---|---|---|---|---|---|---|---|
| 232 | H | CH₃ | H | H | —CO-cyclopropyl | —CH₂— | 3-NO₂-phenyl | 112° C. |
| 233 | H | CH₃ | H | H | —CO-cyclopropyl | —CH₂— | 2-chloro-5-methylthiazol-yl | 150° C. |
| 234 | H | CH₃ | H | H | —CO—CHCH₃—Cl | —CH₂— | 3-NO₂-phenyl | 111° C. |
| 235 | H | CH₃ | H | H | —CO—CHCH₃—Cl | —CH₂— | 2-chloro-5-methylthiazol-yl | 109° C. |
| 236 | H | CF₃ | H | H | —CO—CF₃ | —CH₂— | 2-chloro-5-methylthiazol-yl | 112° C. |
| 237 | H | CF₃ | H | H | —CO—C(CH₃)₃ | —CH₂— | 2-chloro-5-methylthiazol-yl | 114° C. |
| 238 | H | CF₃ | H | H | —CO-(2-chloropyridin-3-yl) | —CH₂— | 2-chloro-5-methylthiazol-yl | 86° C. |
| 239 | H | CH₃ | H | H | —CO-cyclobutyl | —CH₂— | 3-CF₃-phenyl | 107° C. |
| 240 | H | CF₃ | H | H | —COOC₂H₅ | —CH₂— | 2-chloro-5-methylthiazol-yl | 127° C. |

TABLE 2-continued $$\text{(I)} \quad \text{or} \quad \text{(IA)}$$

| Ex. No. | R¹ | R² | R³ | R⁴ | R⁵ or R⁵' | A | Z | Melting point or ¹H-NMR* |
|---|---|---|---|---|---|---|---|---|
| 241 | H | CH₃ | H | H | —CO—CF₃ | —CH₂— | 2,4-dichlorophenyl | 98° C. |
| 242 | H | CH₃ | H | H | —CO—C(CH₃)₂C₂H₅ | —CH₂— | 3-CF₃-phenyl | 46° C. |
| 243 | H | CH₃ | H | H | —CO—CH=CH₂ | —CH₂— | 3-CF₃-phenyl | 68° C. |
| 244 | H | CH₃ | H | H | —CO—CH(CH₃)OC₆H₅ | —CH₂— | 3-CF₃-phenyl | 103° C. |
| 245 | H | CH₃ | H | H | —CO—CF₃ | —CH₂— | 3-OCF₃-phenyl | 98° C. |
| 246 | H | CH₃ | H | H | —CO—C(CH₃)₃ | —CH₂— | 3-OCF₃-phenyl | 101° C. |
| 247 | H | Cl | H | H | —COOC₂H₅ | —CH₂— | 3-NO₂-phenyl | 128° C. |
| 248 | H | Cl | H | H | —CO—CF₃ | —CH₂— | 3-CN-phenyl | 137° C. |

TABLE 2-continued

Structures (I) and (IA) shown with substituents R¹, R², R³, R⁴, R⁵ or R⁵′, A, Z.

| Ex. No. | R¹ | R² | R³ | R⁴ | R⁵ or R⁵′ | A | Z | Melting point or ¹H-NMR* |
|---|---|---|---|---|---|---|---|---|
| 249 | H | Cl | H | H | —CO—C(CH₃)₃ | —CH₂— | 3-CN-phenyl | 126° C. |
| 250 | H | Cl | H | H | —COOC₂H₅ | —CH₂— | 3-CN-phenyl | 102° C. |
| 251 | H | CH₃ | H | H | —CO-cyclopentyl | —CH₂ | 3-CF₃-phenyl | 95° C. |
| 252 | H | CH₃ | H | H | —CO—CF₃ | —CH₂— | 3-SO₂CH₃-phenyl | 105° C. |
| 253 | H | CH₃ | H | H | —CO-cyclopropyl | —CH₂ | 3-OCF₃-phenyl | 72° C. |
| 254 | H | H | H | H | —CO-cyclopropyl | —CH₂ | 3-CF₃-phenyl | 101° C. |
| 255 | H | CH₃ | H | H | —CO-cyclopropyl | —CH₂ | 3-F-phenyl | 73° C. |
| 256 | H | Cl | H | H | —CO-cyclopropyl | —CH₂ | 4-methyl-2-chloro-thiazol-5-yl | 148° C. |

TABLE 2-continued

| Ex. No. | R¹ | R² | R³ | R⁴ | R⁵ or R⁵' | A | Z | Melting point or ¹H-NMR* |
|---|---|---|---|---|---|---|---|---|
| 257 | H | CH₃ | H | H | —CO-△ | —CH₂ | 3-CN-phenyl | 74° C. |
| 258 | H | H | CH₃ | H | —CO-△ | —CH₂ | 3-CF₃-phenyl | |
| 259 | H | CH₃ | H | H | —CO-△ | —CH₂ | 3,4-diCl-phenyl | |
| 260 | H | CH₃ | H | H | —CO-△ | —CH₂ | 4-F-phenyl | |
| 261 | H | H | H | H | —CO-△ | —CH₂ | methylthiazolyl-Cl | |
| 262 | H | CH₃ | H | H | —CO-△ | —CH₂ | 2-Cl-5-NO₂-phenyl (methyl) | 173° C. |
| 263 | H | CF₃ | H | H | —CO-△ | —CH₂ | isopropylthiazolyl-Cl | 124° C. |

*Unless otherwise stated, the ¹-NMR spectra were recorded in deuterochloroform (CDCl₃) with tetramethylsilane (TMS) as the internal standard. The chemical shift is indicated as δ value in ppm.

PREPARATION OF THE STARTING COMPOUND

Examples II-I

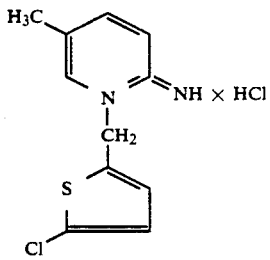

3.2 g (0.03 mol) of 2-amino-5-methylpyridine are dissolved in 100 ml of acetonitrile, and 5 g (0.03 mol) of 2-chloro-5-chloromethylthiophene are added. The mixture is stirred for 8 hours at 60° C. and for 18 hours at room temperature. The solid which has formed is filtered off with suction and dried. 1.6 g (20% of theory) of N-(5-chlorothien-2-yl-methyl)-5-methyl-2-iminopyridine hydrochloride of melting point 208° C. are obtained.

The compounds of the formula (II), which are listed in Table 3, are obtained in a corresponding manner and following the general preparation instructions.

TABLE 3

| Ex. No. | $R^1$ | $R^2$ | $R^3$ | $R^4$ | A | Z | HX | Melting point or $^1$H-NMR* |
|---|---|---|---|---|---|---|---|---|
| II-2 | H | $CH_3$ | H | H | $-CH_2-$ | 2,3-dichlorophenyl | HCl | 248° C. |
| II-3 | H | H | H | H | $-CH_2-$ | 3,5-dichlorophenyl | HCl | decomp. 218° C. |
| II-4 | H | H | H | H | $-CH_2-$ | 2-chlorophenyl | HCl | δ = 5.59 |
| II-5 | H | $CH_3$ | H | H | $-CH_2-$ | 2-nitrophenyl | HCl | 250° C. |
| II-6 | H | $CH_3$ | H | H | $-CH_2-$ | 4-fluorophenyl | HCl | 172° C. |
| II-7 | H | $CH_3$ | H | H | $-CH_2-$ | 3-trifluoromethylphenyl | HCl | 195-197° C. |

TABLE 3-continued

[Structure: pyridine-type ring with R² at position 5, R³ at position 4, R⁴ at position 3, R¹ at position 6, N at position 1 with A-Z substituent, =NH at position 2, × HX]

| Ex. No. | R¹ | R² | R³ | R⁴ | A | Z | HX | Melting point or $^1$H-NMR* |
|---|---|---|---|---|---|---|---|---|
| II-8 | H | Cl | H | H | —CH₂— | 2,4-dichlorophenyl | HCl | δ = 5.51 |
| II-9 | H | H | H | H | —CH₂— | 3-(CF₃)phenyl | HCl | 180° C. |
| II-10 | H | Cl | H | H | —CH₂— | 3-(CF₃)phenyl | HCl | δ = 5.65 |
| II-11 | H | CH₃ | H | H | —CH₂— | 2-chlorophenyl | HCl | δ = 5.57 |
| II-12 | H | CH₃ | H | H | —CH₂— | 3-methoxyphenyl | HCl | 155° C. |
| II-13 | H | CH₃ | H | H | —CH₂— | 3-fluorophenyl | HCl | δ = 5.59 |
| II-14 | H | CH₃ | H | H | —CH₂— | 2,4-difluorophenyl | HCl | 239° C. |
| II-15 | H | CH₃ | H | H | —CH₂— | phenyl | HBr | 216° C. |
| II-16 | H | H | CH₃ | H | —CH₂— | 3-(CF₃)phenyl | HCl | δ = 5.61 |

TABLE 3-continued
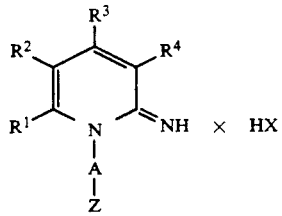
| Ex. No. | R¹ | R² | R³ | R⁴ | A | Z | HX | Melting point or ¹H-NMR* |
|---|---|---|---|---|---|---|---|---|
| II-17 | H | CH₃ | H | H | —CH₂— | 3-CH₃-C₆H₄ | HCl | δ = 5.42 |
| II-18 | H | H | H | H | —CH₂— | 3-Cl-C₆H₄ | HCl | δ = 5.55 |
| II-19 | H | H | H | H | —CH₂— | 4-F-C₆H₄ | HCl | δ = 5.59 |
| II-20 | H | CH₃ | H | H | —CH₂— | 4-CF₃-C₆H₄ | HCl | 240° C. |
| II-21 | H | CH₃ | H | H | —CH₂— | 2-CF₃-C₆H₄ | HCl | 230° C. |
| II-22 | H | CH₃ | H | H | —CH₂— | 3,4-Cl₂-C₆H₃ | HCl | δ = 5.52 |
| II-23 | H | CH₃ | H | H | —CH₂— | 3-Cl-5-CF₃-C₆H₃ | HCl | δ = 5.59 |
| II-24 | H | CH₃ | H | H | —CH₂— | 3-CF₃-4-Cl-C₆H₃ | HCl | δ = 5.62 |
| II-25 | H | CH₃ | H | H | —CH₂— | 2-Cl-3-CF₃-C₆H₃ | HCl | δ = 5.59 |

TABLE 3-continued

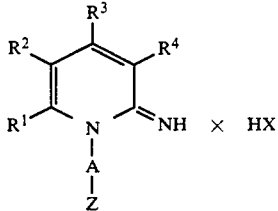

| Ex. No. | R¹ | R² | R³ | R⁴ | A | Z | HX | Melting point or ¹H-NMR* |
|---|---|---|---|---|---|---|---|---|
| II-26 | H | H | H | H | —CH₂— | 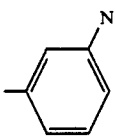 3-NO₂-phenyl | HCl | 212° C. |
| II-27 | H | CH₃ | H | H | —CH₂— | 3-phenoxy-phenyl | HCl | 210° C. |
| II-28 | H | CH₃ | H | H | —CH₂— | 2,4-dichlorophenyl | HCl | 280° C. |
| II-29 | H | CH₃ | H | H | —CH₂— | 2-chloro-5-methylthiazolyl | HCl | δ = 5.82 |
| II-30 | H | H | CH₃ | H | —CH₂— | 2-chloro-5-methylthiazolyl | HCl | 112° C. |
| II-31 | H | H | H | —CH₃ | —CH₂— | 2-chloro-5-methylthiazolyl | HCl | 204° C. |
| II-32 | H | Cl | H | H | —CH₂— | 2-chloro-5-methylthiazolyl | HCl | 230° C. |
| II-33 | H | H | H | H | —CH₂— | 2-chloro-5-methylthiazolyl | HCl | δ = 5.86 |
| II-34 | H | CH₃ | H | H | —CH₂— | 2-chlorophenyl | HCl | δ = 5.50 |

TABLE 3-continued
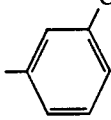
| Ex. No. | R¹ | R² | R³ | R⁴ | A | Z | HX | Melting point or ¹H-NMR* |
|---|---|---|---|---|---|---|---|---|
| II-35 | H | Cl | H | H | —CH₂— | 3-Cl-phenyl | HCl | δ = 5.59 |
| II-36 | H | Cl | H | H | —CH₂— | 4-F-phenyl | HCl | δ = 5.45 |
| II-37 | H | CH₃ | H | H | —CH₂— | 3,5-bis(CF₃)-phenyl | HCl | δ = 5.77 |
| II-38 | H | CH₃ | H | H | —CH₂— | 2-chloropyridin-5-yl | HCl | Oil |
| II-39 | H | H | H | H | —CH₂— | 3-chloro-5-isothiazolyl | HBr | Oil |
| II-40 | H | CH₃ | H | H | —CH₂— | 3-COOCH₃-phenyl | HCl | 200° C. |
| II-41 | H | Cl | H | H | —CH₂— | 3-F-phenyl | HCl | 168° C. |
| II-42 | H | CF₃ | H | H | —CH₂— | 3-CF₃-phenyl | HCl | 265° C. |
| II-43 | H | Cl | H | H | —CH₂— | 3-NO₂-phenyl | HCl | 261° C. |

TABLE 3-continued

Structure:

R² at position 5, R³ at position 4, R⁴ at position 3, R¹ at position 6, with N-A-Z substituent, and =NH × HX at position 2.

| Ex. No. | R¹ | R² | R³ | R⁴ | A | Z | HX | Melting point or ¹H-NMR* |
|---|---|---|---|---|---|---|---|---|
| II-44 | H | CH₃ | H | H | —CH₂— | 3-bromophenyl | HBr | 218° C. |
| II-45 | H | CH₃ | H | H | —CH₂— | 3-cyanophenyl | HCl | 233° C. |
| II-46 | H | CH₃ | H | H | —CH₂— | 2-methoxy-4-nitrophenyl | HCl | 222° C. |
| II-47 | H | CF₃ | H | H | —CH₂— | 2-chloro-4-methylthiazol-5-yl | HCl | 201° C. |
| II-48 | H | CH₃ | H | H | —CH₂— | 2,4-dichlorophenyl | HCl | 225° C. |
| II-49 | H | CH₃ | H | H | —CH₂— | phenyl | HCl | 106° C. |

*The ¹H-NMR spectra were recorded in dimethyl sulphoxide (DMSO) with tetramethylsilane (TMS) as the internal standard. The chemical shift is indicated as δ value in ppm.

USE EXAMPLES

In the following Use Examples, the compound given below was employed as comparison substance:

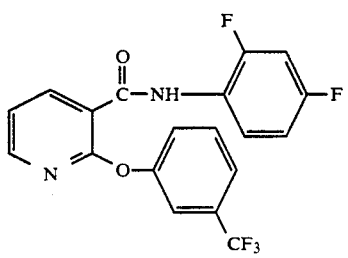

(A)

N-(2,4-difluorophenyl)-2-[3-(trifluoromethyl)phenoxy]-3-pyridinecarboxamide (disclosed in EP-A 53,011/compound No. 3).

EXAMPLE A

Post-emergence Test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5-15 cm are sprayed with the preparation of the active compound in such a way as to apply the particular amounts of active compound desired per unit area. The concentration of the spray liquor is so chosen that the particular amounts of active compound desired are applied in 1,000 l of water/ha. After three weeks, the degree of damage to the plants is rated in % damage in comparison to the development of the untreated control. The figures denote:

0% = no action (like untreated control)
100% = total destruction

In this test, a clearly superior activity compared with the comparison substance (A) is shown, for example, by the compounds of Preparation Examples 15, 13, 26, 33, 71, 77, 113, 157, 187 and 202.

EXAMPLE B

Pre-emergence Test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0% = no action (like untreated control)
100% = total destruction

In this test, a clearly superior activity compared with the comparison substance (A) is shown, for example, by the compounds of the following Preparation Examples: 1, 2, 3, 13, 15, 26, 28, 33, 43, 47, 50, 77, 105, 125, 128, 130, 131, 139, 148, 157, 164, 165, 167, 173, 178, 180, 181, 184, 187, 188, 190, 193, 202 and 205.

It will be understood that the specification and examples are illustrative but not limitative of the present invention and that other embodiments within the spirit and scope of the invention will suggest themselves to those skilled in the art.

We claim:

1. A method of combating unwanted vegetation which comprises applying to such vegetation or to a locus from which it is desired to exclude such vegetation, a herbicidally effective amount of a 2-iminopyridine of the formula

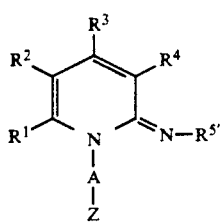

(IA)

in which $R^1$, $R^2$, $R^3$ and $R^4$ independently of one another represent hydrogen, halogen, alkyl, halogenoalkyl, alkoxy, halogenoalkoxy, alkylthio or halogenalkylthio, $R^{5'}$ represents cyano, straight-chain or branched alkylcarbonyl having 1 to 20 carbon atoms in the alkyl moiety, or represents straight-chain or branched alkenylcarbonyl or alkynylcarbonyl each of which has 2 to 20 carbon atoms in the alkenyl or alkynyl moiety, or represents straight-chain or branched halogenoalkylcarbonyl having 1 to 20 carbon atoms in the alkyl moiety and 1 to 41 identical or different halogen atoms, or represents straight-chain or branched halogenoalkenylcarbonyl having 2 to 20 carbon atoms in the alkenyl moiety and 1 to 39 identical or different halogen atoms, or represents straight-chain or branched halogenoalkynylcarbonyl having 2 to 20 carbon atoms in the alkynyl moiety and 1 to 37 identical or different halogen atoms, or represents straight-chain or branched alkoxycarbonyl having 1 to 20 carbon atoms in the alkoxy moiety, or represents phenylcarbonyl, phenoxycarbonyl, phenylaminocarbonyl, phenylmethylcarbonyl, phenylethylcarbonyl, phenylpropylcarbonyl, phenylethenylcarbonyl, phenoxymethylcarbonyl or phenoxyethylcarbonyl, each of which is monosubstituted or polysubstituted by identical or different substituents, the phenyl substituents being selected from the group consisting of halogen, cyano, nitro, straight-chain or branched alkyl having 1 to 4 carbon atoms, straight-chain or branched halogenoalkyl having 1 to 4 carbon atoms and 1 to 9 identical or different halogen atoms, straight-chain or branched alkoxy having 1 to 4 carbon atoms, and also straight-chain or branched halogenoalkoxy having 1 to 4 carbon atoms and 1 to 9 identical or different halogen atoms; or $R^{5'}$ furthermore represents straight-chain or branched alkylsulphonyl having 1 to 4 carbon atoms, or represents alkylaminocarbonyl having 1 to 20 carbon atoms in the straight-chain or branched alkyl moiety, or represents phenylsulphonyl which is either substituted, monosubstituted or polysubstituted by identical or different substituents selected from the group consisting of halogen, cyano, nitro, straight-chain or branched alkyl having 1 to 4 carbon atoms, straight-chain or branched halogenoalkyl having 1 to 4 carbon atoms and 1 to 9 identical or different halogen atoms, straight-chain or branched alkoxy having 1 to 4 carbon atoms, straight-chain or branched halogenoalkoxy having 1 to 4 carbon atoms and 1 to 9 identical or different halogen atoms, and also alkoxycarbonyl having 1 to 4 carbon atoms in the straight-chain or branched alkoxy moiety, or represents cycloalkylcarbonyl having 3 to 6 carbon atoms in the cycloalkyl moiety, or represents straight-chain or branched alkoxyalkylcarbonyl having 1 to 4 carbon atoms in the alkoxy- and alkyl moiety, or represents straight-chain or branched alkylcarbonyloxalkylcarbonyl, or alkoxycarbonylcarbonyl having 1 to 4 carbon atoms in the alkoxy- or alkyl moiety respectively, or represents straight-chain or branched halogenalkylsulphonyl having 1 to 4 carbon atoms and 1 to 9 identical or different halogen atoms, A represents alkanediyl and Z represents phenyl, or thienyl, thiazolyl, isothiazolyl, isoxazolyl or oxa-2,4-diazolyl, each of which is either unsubstituted or monosubstituted or polysubstituted by identical or different substituents selected from the group consisting of nitro, cyano, halogen, straight-chain or branched alkyl having 1 to 4 carbon atoms, straight-chain or branched halogenoalkyl or halogenoalkylthio each of which has 1 to 4 carbon atoms and each of which has 1 to 9 identical or different halogen atoms, straight-chain or branched alkoxy or alkylthio each of which has 1 to 4 carbon atoms, straight-chain or branched halogenoalkoxy having 1 to 4 carbon atoms and 1 to 9 identical or different halogen atoms, straight-chain or branched alkoxycarbonyl having 1 to 4 carbon atoms in the alkoxy moiety, and also phenoxy which is either unsubstituted or monosubstituted or polysubstituted by identical or different substituents from the group consisting of halogen, $C_1$-$C_4$-alkyl or halogeno-$C_1$-$C_4$-alkyl.

2. The method according to claim 1, in which $R^1$, $R^2$, $R^3$ and $R^4$ independently of one another represent hydrogen, halogen, straight-chain or branched alkyl having 1 to 4 carbon atoms, straight-chain or branched halogenoalkyl having 1 to 4 carbon atoms and 1 to 9 identical or different halogen atoms, straight-chain or branched alkoxy or alkylthio having 1 to 4 carbon atoms, or straight-chain or branched halogenoalkyl or halogenalkylthio having 1 to 4 carbon atoms and 1 to 9 identical or different halogen atoms, $R^{5'}$ represents cyano, straight-chain or branched alkylcarbonyl having 1 to 20 carbon atoms in the alkyl moiety, or represents straight-chain or branched alkenylcarbonyl or alkynylcarbonyl each of which has 2 to 20 carbon atoms in the alkenyl or alkynyl moiety, or represents straight-chain or branched halogenoalkylcarbonyl having 1 to 20 carbon atoms in the alkyl moiety and 1 to 41 identical or different halogen atoms, or represents straight-chain or branched halogenoalkenylcarbonyl having 2 to 20 carbon atoms in the alkenyl moiety and 1 to 39 identical or different halogen atoms, or represents straight-chain or branched halogenoalkynylcarbonyl having 2 to 20 carbon atoms in the alkynyl moiety and 1 to 37 identical or different halogen atoms, or represents straight-chain or branched alkoxycarbonyl having 1 to 20 carbon atoms in the alkoxy moiety, or represents phenylcarbonyl, phenoxycarbonyl, phenylaminocarbonyl, phenylmethylcarbonyl, phenylethylcarbonyl, phenylpropylcarbonyl, phenylethenylcarbonyl, phenoxymethylcarbonyl or phenoxyethylcarbonyl, each of which is monosubstituted or polysubstituted by identical or different substituents, the phenyl substituents being selected from the group consisting of halogen, cyano, nitro, straight-chain or branched alkyl having 1 to 4 carbon atoms, straight-chain or branched halogenoalkyl having 1 to 4 carbon atoms and 1 to 9 identical or different halogen atoms, straight-chain or branched alkoxy having 1 to 4 carbon atoms, and also straight-chain or branched halogenoalkoxy having 1 to 4 carbon atoms and 1 to 9 identical or different halogen atoms; or $R^{5'}$ furthermore represents straight-chain or branched alkylsulphonyl having 1 to 4 carbon atoms, or represents alkylaminocarbonyl having 1 to 20 carbon atoms in the straight-chain or branched alkyl moiety, or represents phenylsulphonyl which is either substituted, monosubstituted or polysubstituted by identical or different substituents selected from the group consisting of halogen, cyano, nitro, straight-chain or branched alkyl having 1 to 4 carbon atoms, straight-chain or branched halogenoalkyl having 1 to 4 carbon atoms and 1 to 9 identical or different halogen atoms, straight-chain or branched alkoxy having 1 to 4 carbon atoms, straight-chain or branched halogenoalkoxy having 1 to 4 carbon atoms and 1 to 9 identical or different halogen atoms, and also alkoxycarbonyl having 1 to 4 carbon atoms in the straight-chain or branched alkoxy moiety, or represents cycloalkylcarbonyl having 3 to 6 carbon atoms in the cycloalkyl moiety, or represents straight-chain or branched alkoxyalkylcarbonyl having 1 to 4 carbon atoms in the alkoxy- and alkyl moiety, or represents straight-chain or branched alkylcarbonyloxalkylcarbonyl, or alkoxycarbonylcarbonyl having 1 to 4 carbon atoms in the alkoxy- or alkyl moiety respectively, or represents straight-chain or branched halogenalkylsulphonyl having 1 to 4 carbon atoms and 1 to 9 identical or different halogen atoms, A represents straight-chain or branched alkanediyl having 1 to 4 carbon atoms, and Z represents phenyl, or thienyl, thiazolyl, isothiazolyl, isoxazolyl or oxa-2,4-diazolyl, each of which is either unsubstituted or monosubstituted or polysubstituted by identical or different substituents selected from the group consisting of nitro, cyano, halogen, straight-chain or branched alkyl having 1 to 4 carbon atoms, straight-chain or branched halogenoalkyl or halogenoalkylthio each of which has 1 to 4 carbon atoms and each of which has 1 to 9 identical or different halogen atoms, straight-chain or branched alkoxy or alkylthio each of which has 1 to 4 carbon atoms, straight-chain or branched halogenoalkoxy having 1 to 4 carbon atoms and 1 to 9 identical or different halogen atoms, straight-chain or branched alkoxycarbonyl having 1 to 4 carbon atoms in the alkoxy moiety, and also phenoxy which is either unsubstituted or monosubstituted or polysubstituted by identical or different substituents from the group consisting of halogen, $C_1$-$C_4$-alkyl or halogeno-$C_1$-$C_4$-alkyl.

3. The method according to claim 1, in which $R^1$ represents hydrogen, $R^2$ represents hydrogen, fluorine, chlorine, bromine, methyl, ethyl or trifluoromethyl, $R^3$ represents hydrogen, methyl, ethyl or trifluoromethyl, $R^4$ represents hydrogen;

$R^{5'}$ represents cyano, straight-chain or branched alkylcarbonyl having 1 to 10 carbon atoms in the alkyl moiety, or represents straight-chain or branched alkenylcarbonyl or alkinylcarbonyl each of which has 2 to 10 carbon atoms in the alkenyl or alkynyl moiety, or represents straight-chain or branched halogenalkylcarbonyl having 1 to 10 carbon atoms and 1 to 21 fluorine plus chlorine atoms, or represents straight-chain or branched halogenalkenylcarbonyl having 2 to 10 carbon atoms in the alkenyl moiety and 1 to 19 fluorine plus chlorine atoms, straight-chain or branched alkynylcarbonyl having 2 to 10 carbon atoms in the alkynyl moiety and 1 to 17 fluorine plus chlorine atoms, or represents straight-chain or branched alkoxycarbonyl having 1 to 10 carbon atoms in the alkoxy moiety, or represents straight-chain or branched alkylthiocarbonyl having 1 to 10 carbon atoms in the alkyl moiety, or represents phenylcarbonyl, phenoxycarbonyl, phenylaminocarbonyl, phenylmethylcarbonyl, phenylethylcarbonyl, phenylpropylcarbonyl, phenylethenylcarbonyl, phenoxymethylcarbonyl or phenoxyethylcarbonyl, each of which is unsubstituted, monosubstituted or disubstituted by identical or different substituents from the group consisting of fluorine, chlorine, bromine, cyano, nitro, methyl, trifluoromethyl and methoxy, or represents methylsulphonyl or ethylsulphonyl, or represents straight-chain or branched alkylaminocarbonyl having 1 to 10 carbon atoms in the alkyl moiety, or represents phenylsulphonyl which is unsubstituted, monosubstituted or disubstituted by identical or different substituents from the group consisting of fluorine, chlorine, cyano, nitro, methyl, trifluoromethyl, methoxycarbonyl and ethoxycarbonyl, or represents $C_3$-$C_6$-cycloalkylcarbonyl, methoxyacetyl, acetyloxyacetyl or triflourmethylsulphonyl, A represents methanediyl or ethanediyl and Z represents phenyl, thienyl, thiazolyl, isothiazolyl, isoxazolyl or oxa-2,4-diazolyl each of which is unsubstituted, monosubstituted or disubstituted by identical or different substituents selected from the group consisting of nitro, cyano, fluorine, chlorine, bromine, methyl, ethyl, trifluoromethyl, difluoromethyl, methylthio, trifluoromethylthio, difluoromethylthio, methoxy, ethoxy, trifluoromethoxy, difluoromethoxy, methoxycarbonyl, ethoxycarbonyl and phenoxy.

4. A 2-iminopyridine of the formula

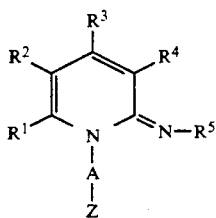

(I)

in which $R^1$, $R^2$, $R^3$ and $R^4$ independently of one another represent hydrogen, halogen, alkyl, halogenoalkyl, alkoxy, halogenoalkoxy, alkylthio or halogenalkylthio, $R^5$ represents straight-chain or branched alkylcarbonyl having 1 to 20 carbon atoms in the alkyl moiety, or represents straight-chain or branched alkenylcarbonyl or alkynylcarbonyl each of which has 2 to 20 carbon atoms in the alkenyl or alkinyl moiety, or represents straight-chain or branched halogenoalkylcarbonyl having 1 to 20 carbon atoms in the alkyl moiety and 1 to 41 identical or different halogen atoms, or represents straight-chain or branched halogenoalkenylcarbonyl having 2 to 20 carbon atoms in the alkenyl moiety and 1 to 39 identical or different halogen atoms, or represents straight-chain or branched halogenoalknylcarbonyl having 2 to 20 carbon atoms in the alkinyl moiety and 1 to 37 identical or different halogen atoms, or represents straight-chain or branched alkoxycarbonyl having 1 to 20 carbon atoms in the alkoxy moiety, or represents straight-chain or branched alkylthiocarbonyl having 1 to 20 carbon atoms in the alkylthio moiety, or represents phenylcarbonyl, phenoxycarbonyl, phenylaminocarbonyl, phenylmethylcarbonyl, phenylethylcarbonyl, phenylpropylcarbonyl, phenylethenylcarbonyl, furylcarbonyl, thienylcarbonyl, pyridylcarbonyl, phenoxymethylcarbonyl or phenoxyethylcarbonyl, each of which is substituted, monosubstituted or polysubstituted by identical or different substituents selected from the group consisting of halogen, cyano, nitro, straight-chain or branched alkyl having 1 to 4 carbon atoms, straight-chain or branched halogenoalkyl having 1 to 4 carbon atoms and 1 to 9 identical or different halogen atoms, straight-chain or branched alkoxy having 1 to 4 carbon atoms, and also straight-chain or branched halogenoalkoxy having 1 to 4 carbon atoms and 1 to 9 identical or different halogen atoms; or $R^5$ furthermore represents straight-chain or branched alkylsulphonyl having 1 to 4 carbon atoms, or represents alkylaminocarbonyl having 1 to 20 carbon atoms in the straight-chain or branched alkyl moiety, or represents phenylsulphonyl which is unsubstituted, monosubstituted or polysubstituted by identical or different substituents selected from the group consisting of halogen, cyano, nitro, straight-chain or branched alkyl having 1 to 4 carbon atoms, straight-chain or branched halogenoalkyl having 1 to 4 carbon atoms and 1 to 9 identical or different halogen atoms, straight-chain or branched alkoxy having 1 to 4 carbon atoms, straight-chain or branched halogenoalkoxy having 1 to 4 carbon atoms and 1 to 9 identical or different halogen atoms and alkoxycarbonyl having 1 to 4 carbon atoms in the straight-chain or branched alkoxy moiety, or represents cycloalkylcarbonyl having 3 to 6 carbon atoms in the cycloalkyl moiety, or represents straight-chain or branched alkoxyalkylcarbonyl having in each case 1 to 4 carbon atoms in the alkoxy- and alkyl moiety, or represents in each case straight-chain or branched alkylcarbonyloxalkylcarbonyl or alkoxycarbonylcarbonyl having 1 to 4 carbon atoms in the alkoxy- or alkyl moiety respectively, or represents straight-chain or branched halogenalkylsulphonyl having 1 to 4 carbon atoms and 1 to 9 identical or different halogen atoms, A represents alkanediyl and Z represents phenyl, thienyl, thiazolyl, isothiazolyl, isoxazolyl or oxa-2,4-diazolyl, each of which is unsubstituted, monosubstituted or polysubstituted by identical or different substituents selected from the group consisting of nitro, cyano, halogen, straight-chain or branched-alkyl having 1 to 4 carbon atoms, in each case straight-chain or branched halogenoalkyl or halogenoalkylthio each of which has 1 to 4 carbon atoms and each of which has 1 to 9 identical or different halogen atoms, in each case straight-chain or branched alkoxy or alkylthio each of which has 1 to 4 carbon atoms, straight-chain or branched halogenoalkoxy having 1 to 4 carbon atoms and 1 to 9 identical or different halogen atoms, straight-chain or branched alkoxycarbonyl having 1 to 4 carbon atoms in the alkoxy moiety and phenoxy which is unsubstituted, monosubstituted or polysubstituted by identical or different substituents from the group consisting of halogen, $C_1$-$C_4$-alkyl and halogeno-$C_1$-$C_4$-alkyl.

5. A 2-iminopyridine according to claim 4, in which
$R^1$, $R^2$, $R^3$ and $R^4$ independently of one another represent hydrogen, halogen, straight-chain or branched alkyl having 1 to 4 carbon atoms, straight-chain or branched halogenoalkyl having 1 to 4 carbon atoms and 1 to 9 identical or different halogen atoms, in each case straight-chain or branched alkoxy or alkylthio having 1 to 4 carbon atoms, or in each case or straight-chain or branched halogenoalkoxy or halogenalkylthio having 1 to 4 carbon atoms and 1 to 9 identical or different halogen atoms, $R^5$ represents straight-chain or branched alkylcarbonyl having 1 to 20 carbon atoms in the alkyl moiety, or represents straight-chain or branched alkenylcarbonyl or alkynylcarbonyl each of which has 2 to 20 carbon atoms in the alkenyl or alkinyl moiety, or represents straight-chain or branched halogenoalkylcarbonyl having 1 to 20 carbon atoms in the alkyl moiety and 1 to 41 identical or different halogen atoms, or represents straight-chain or branched halogenoalkenylcarbonyl having 2 to 20 carbon atoms in the alkenyl moiety and 1 to 39 identical or different halogen atoms, or represents straight-chain or branched halogenoalknylcarbonyl having 2 to 20 carbon atoms in the alkinyl moiety and 1 to 37 identical or different halogen atoms, or represents straight-chain or branched alkoxycarbonyl having 1 to 20 carbon atoms in the alkoxy moiety, or represents straight-chain or branched alkylthiocarbonyl having 1 to 20 carbon atoms in the alkylthio moiety, or represents phenylcarbonyl, phenoxycarbonyl, phenylaminocarbonyl, phenylmethylcarbonyl, phenylethylcarbonyl, phenylpropylcarbonyl, phenylethenylcarbonyl, furylcarbonyl, thienylcarbonyl, pyridylcarbonyl, phenoxymethylcarbonyl or phenoxyethylcarbonyl, each of which is substituted, monosubstituted or polysubstituted by identical or different substituents selected from the group consisting of halogen, cyano, nitro, straight-chain or branched alkyl having 1 to 4 carbon atoms, straight-chain or branched halogenoalkyl having 1 to 4 carbon atoms and 1 to 9 identical or different halogen atoms, straight-chain or branched alkoxy having 1 to 4 carbon atoms, and also straight-chain or branched halogenoalkoxy having 1 to 4 carbon atoms and 1 to 9 identical or different halogen atoms; or $R^5$ furthermore represents straight-chain or branched alkylsulphonyl having 1 to 4 carbon atoms, or represents alkylaminocarbonyl having 1 to 20 carbon atoms in the straight-chain or branched alkyl moiety, or represents phenylsulphonyl which is unsubstituted, monosubstituted or polysubstituted by identical or different substituents selected from the group consisting of halogen, cyano, nitro, straight-chain or branched alkyl having 1 to 4 carbon atoms, straight-chain or branched halogenoalkyl having 1 to 4 carbon atoms and 1 to 9 identical or different halogen atoms, straight-chain or branched alkoxy having 1 to 4 carbon atoms, straight-chain or branched halogenoalkoxy having 1 to 4 carbon atoms and 1 to 9 identical or different halogen atoms and alkoxycarbonyl having 1 to 4 carbon atoms in the straight-chain or branched alkoxy moiety, or represents cycloalkylcarbonyl having 3 to 6 carbon atoms in the cycloalkyl moiety, or represents straight-chain or branched alkoxyalkylcarbonyl having in each case 1 to 4 carbon atoms in the alkoxy- and alkyl moiety, or represents in each case straight-chain or branched alkylcarbonyloxalkylcarbonyl or alkoxycarbonylcarbonyl having 1 to 4 carbon atoms in the alkoxy- or alkyl moiety respectively, or represents straight-chain or branched halogenalkylsulphonyl having 1 to 4 carbon atoms and 1 to 9 identical or different halogen atoms, A represents straight-chain or branched alkanediyl having 1 to 4 carbon atoms and Z represents phenyl, thienyl, thiazolyl, isothiazolyl, isoxazolyl or oxa-2,4-diazolyl, each of which is unsubstituted, monosubstituted or polysubstituted by identical or different substituents selected from the group consisting of nitro, cyano, halogen, straight-chain or branched alkyl having 1 to 4 carbon atoms, in each case straight-chain or branched halogenoalkyl or halogenoalkylthio each of which has 1 to 4 carbon atoms and each of which has 1 to 9 identical or different halogen atoms, in each case straight-chain or branched alkoxy or alkylthio each of which has 1 to 4 carbon atoms, straight-chain or branched halogenoalkoxy having 1 to 4 carbon atoms and 1 to 9 identical or different halogen atoms, straight-chain or branched alkoxycarbonyl having 1 to 4 carbon atoms in the alkoxy moiety and phenoxy which is unsubstituted, monosubstituted or polysubstituted by identical or different substituents from the group consisting of halogen, $C_1$-$C_4$-alkyl and halogeno-$C_1$-$C_4$-alkyl.

* * * * *